US008703136B2

(12) United States Patent
Baas et al.

(10) Patent No.: US 8,703,136 B2
(45) Date of Patent: Apr. 22, 2014

(54) COMPLEMENT INHIBITION FOR IMPROVED NERVE REGENERATION

(75) Inventors: Frank Baas, Hilversum (NL); Valeria Ramaglia, Amsterdam (NL)

(73) Assignee: Regenesance B.V., Amsterdam (NL)

( * ) Notice: Subject to any disclaimer, the term of this patent is extended or adjusted under 35 U.S.C. 154(b) by 1041 days.

(21) Appl. No.: 12/445,037

(22) PCT Filed: Oct. 10, 2007

(86) PCT No.: PCT/NL2007/050490
§ 371 (c)(1),
(2), (4) Date: Feb. 17, 2010

(87) PCT Pub. No.: WO2008/044928
PCT Pub. Date: Apr. 17, 2008

(65) Prior Publication Data
US 2010/0143344 A1    Jun. 10, 2010

Related U.S. Application Data

(60) Provisional application No. 60/850,277, filed on Oct. 10, 2006.

(51) Int. Cl.
*A61K 39/395* (2006.01)

(52) U.S. Cl.
USPC ................................ 424/139.1; 514/18.2

(58) Field of Classification Search
None
See application file for complete search history.

(56) References Cited

U.S. PATENT DOCUMENTS

| 5,679,345 | A | 10/1997 | Sanfilippo et al. |
| 6,248,365 | B1 | 6/2001 | Romisch et al. |
| 2002/0168352 | A1 | 11/2002 | Winkler et al. |
| 2006/0233776 | A1 | 10/2006 | Heimburger et al. |
| 2006/0292141 | A1 | 12/2006 | Holers et al. |
| 2007/0004625 | A1 | 1/2007 | Li et al. |
| 2007/0185011 | A1 | 8/2007 | Nuijens |
| 2008/0305993 | A1 | 12/2008 | Mannesse et al. |

FOREIGN PATENT DOCUMENTS

| AU | B-44778/93 | 8/1993 |
| EP | 0983304 B1 | 3/2000 |
| EP | 1 674 580 A1 | 6/2006 |
| EP | 1774972 A1 | 4/2007 |
| JP | 2004-536138 | 12/2004 |
| JP | 2007-8876 | 1/2007 |
| JP | 2008-542298 | 11/2008 |
| JP | 2010-502686 | 1/2010 |
| WO | WO-91/06650 | 5/1991 |
| WO | 91/15221 A1 | 10/1991 |
| WO | WO-92/22320 | 12/1992 |
| WO | 95/06479 A1 | 3/1995 |
| WO | 95/23512 A1 | 9/1995 |
| WO | 95/23856 A1 | 9/1995 |
| WO | 97/13786 A1 | 4/1997 |
| WO | 97/17987 A1 | 5/1997 |
| WO | 99/10009 A1 | 3/1999 |
| WO | 99/21581 A1 | 5/1999 |
| WO | 99/37149 A1 | 7/1999 |
| WO | 99/44625 A1 | 9/1999 |
| WO | WO-00/29033 | 5/2000 |
| WO | 00/35483 A1 | 6/2000 |
| WO | 00/47194 A2 | 8/2000 |
| WO | 00/64473 A1 | 11/2000 |
| WO | 03/009803 A2 | 2/2003 |
| WO | 03/066805 A2 | 8/2003 |
| WO | 2004/045520 A2 | 6/2004 |
| WO | 2004/075837 A2 | 9/2004 |
| WO | 2005/002627 A2 | 1/2005 |
| WO | WO-2005/016285 A2 | 2/2005 |
| WO | 2005/025509 A2 | 3/2005 |
| WO | 2005/074607 A2 | 8/2005 |
| WO | 2005/077417 A1 | 8/2005 |
| WO | 2005/092366 A1 | 10/2005 |
| WO | 2005/110481 A2 | 11/2005 |
| WO | 2006/103118 A2 | 10/2006 |
| WO | WO-2006/128006 A1 | 11/2006 |
| WO | 2006/131874 A2 | 12/2006 |
| WO | 2007/047995 A2 | 4/2007 |
| WO | 2007/056227 A2 | 5/2007 |
| WO | 2007/103134 A2 | 9/2007 |
| WO | 2007/145806 A2 | 12/2007 |
| WO | 2008/029167 A1 | 3/2008 |
| WO | WO-2008/044928 A1 | 4/2008 |
| WO | 2008/069889 A2 | 6/2008 |
| WO | 2008/097525 A2 | 8/2008 |
| WO | 2008/113834 A2 | 9/2008 |
| WO | 2008/118711 A2 | 10/2008 |

(Continued)

OTHER PUBLICATIONS

Jackowski, British Journal of Neurosurgery 9 (1995): 303-317.*

(Continued)

*Primary Examiner* — Robert C Hayes
(74) *Attorney, Agent, or Firm* — Nelson Mullins Riley & Scarborough LLP; Jane E. Remillard, Esq.; Jeanne M. DiGiorgio

(57) ABSTRACT

The present invention relates to methods and medicaments used for treating conditions that require axonal regeneration, e.g. in mammals affected by injury or disease of the central or peripheral nervous system. The medicaments used in these methods facilitate axonal regeneration by inhibition of the complement system. Conditions requiring axonal regeneration that may be treated in accordance with the invention include physical injuries as well as neurodegenerative disorders of the peripheral or central nervous system.

6 Claims, 10 Drawing Sheets

(56) References Cited

FOREIGN PATENT DOCUMENTS

| WO | 2008/153962 A2 | 12/2008 |
|---|---|---|
| WO | 2009/014633 A1 | 1/2009 |
| WO | 2009/015087 A2 | 1/2009 |
| WO | 2009/102488 A2 | 8/2009 |
| WO | 2009/105217 A2 | 8/2009 |
| WO | 2009/108153 A1 | 9/2009 |
| WO | 2009/121065 A2 | 10/2009 |
| WO | 2009/151634 A1 | 12/2009 |
| WO | 2010/022149 A1 | 2/2010 |
| WO | 2010/034514 A2 | 4/2010 |
| WO | 2010/039690 A1 | 4/2010 |
| WO | 2010/054403 A1 | 5/2010 |
| WO | 2010/057084 A1 | 5/2010 |
| WO | 2010/100396 A1 | 9/2010 |
| WO | 2011/107591 A1 | 9/2011 |
| WO | 2011/109338 A1 | 9/2011 |
| WO | 2012/006599 A2 | 1/2012 |

OTHER PUBLICATIONS

Bergamaschini, et al. "Recent Advances in the Use of C1 Inhibitor as a Therapeutic Agent" Molecular Immunology, 2003, pp. 155-158.

Ramaglia, et al. "Soluble Complement Receptor 1(sCR1) Protects the Peripheral Nerve from Early Axon Loss After Injury and Facilitates Regeneration" Abstracts/Molecular Immunology, 44, (2007), p. 3949.

Ramaglia, et al. "The Membrane Attack Complex of the Complement System Is Essential for Rapid Wallerian Degeneration" The Journal of Neuroscience, Jul. 18, 2007, pp. 7663-7672.

Woodruff, et al. "Therapeutic Activity of C5a Receptor Antagonists in a Rat Model of Neurodegeneration" The FASEB Journal, vol. 20, Jul. 2006, pp. 1407-1417.

Biesecker, Gregory et al., "Inhibition of Acute Passive Transfer Experimental Autoimmune Myasthenia Gravis with Fab Antibody to Complement C6," The Journal of Immunology, vol. 142(8):2654-2659 (1989).

Akita, et al. "Protective Effect of C1 Esterase Inhibitor on Reperfusion Injury in the Rat Middle Cerebral Artery Occlusion Model" Neurosurgery, Feb. 2003, vol. 52, No. 2, pp. 395-401.

De Simoni, et al. "Neuroprotection by Complement (C1) Inhibitor in Mouse Transient Brain Ischemia" Journal of Cerebral Blood Flow & Metabolism, 2003, vol. 23, No. 2, pp. 232-239.

Heimann, et al. "C1-esterase inhibitor reduces infarct volume after cortical vein occlusion", Brain Research, 1999, vol. 838, pp. 210-213.

Kirschfink, et al. "C1-inhibitor: an anti-inflammatory reagent with therapeutic potential" Expert Opinion Pharmacother, 2001, vol. 2, No. 7, pp. 1073-1083.

Storini, et al. "C1-inhibitor protects against brain ischemia-reperfusion injury via inhibition recruitment and inflammation", Neurobiology of Disease, 2005, vol. 19, pp. 10-17.

Copland, D.A. et al., "Systemic and local anti-C5 therapy reduces the disease seventy in experimental autoimmune uveoretinitis," Clinical and Experimental Immunology, vol. 159:303-314 (2009).

Frei, Yvonne et al., "Generation of a monoclonal antibody to mouse C5 application in a ELISA assay for detection of anti-C5 antibodies," Molecular and Cellular Probes, vol. 1:141-149 (1987).

Huugen, D. et al., "Inhibition of complement factor C5 protects against anti-myeloperoxidase antibody-mediated glomerulonephritis in mice," Kidney International, vol. 71:646-654 (2007).

Mihai, Sidonia et al., "The Alternative Pathway of Complement Activation Is Critical for Blister Induction in Experimental Epidermolysis Bullosa Acquisita," The Journal of Immunology, vol. 178:6514-6521 (2007).

Nilsson, Kajsa E. et al., "Enhanced susceptibility to low-dose collagen-induced arthritis in CR1/2-deficient female mice—possible role of estrogen on CR1 expression," The FASEB Journal, vol. 23:2450-2458 (2009).

Thurman, Joshua M. et al., "C3a Is Required for the Production of CXC Chemokines by Tubular Epithelial Cells after Renal Ischemia/Reperfusion," The Journal of Immunology, vol. 178:1819-1828 (2007).

Wang, Hao et al., "Inhibition of Terminal Complement Components in Presensitized Transplant Recipients Prevents Antibody-Mediated Rejection Leading to Long-Term Graft Survival and Accommodation," The Journal of Immunology, vol. 179:4451-4463 (2007).

Japanese Office Action for Application No. 2009-532314, 12 pages, dated Sep. 4, 2012.

* cited by examiner

COMPLEMENT INHIBITION FOR IMPROVED NERVE REGENERATION

FIELD OF THE INVENTION

The present invention relates to methods and medicaments used for treating conditions that require axonal regeneration, e.g. in mammals affected by injury or disease of the central or peripheral nervous system. The medicaments used in these methods promote axonal regeneration by inhibition of the complement system.

BACKGROUND OF THE INVENTION

Axon degeneration occurs frequently in many types of chronic neurodegenerative diseases and in injuries to axons caused by toxic, ischemic, or traumatic insults. It may lead to separation of the neuron from its targets, resulting in loss of neuronal function. One model of axon degeneration is the self-destructive process observed at the distal portion of a transected axon upon injury, termed Wallerian degeneration (WD) as first described by Waller (1850). In the process of WD, if a nerve fiber is cut or crushed, the part distal to the injury (i.e. the part of the axon separated from the neuron's cell nucleus) will degenerate. Because most neuronal proteins are synthesised in the soma and carried to the axon by specialised axonal transport systems, degeneration of the transected axons has long been thought to result from starvation of necessary proteins and other materials. However, the discovery of a spontaneously occurring mutant mouse strain, C57BL/Wld$^s$, whose axons survived for as long as weeks after transection suggested that Wallerian degeneration involves an active and regulated auto-destruction program.

Indeed one of the most striking cellular responses during WD in the peripheral nervous system (PNS) is the proliferation and infiltration of macrophages (Bruck, 1997). Macrophages participate in a wide array of cellular responses during WD. Once activated, they release factors that are mitogenic for Schwann cells (Baichwal et al., 1988). The completion of WD relies on the phagocytic ability of macrophages to degrade myelin and axonal debris (Griffin et al., 1992). In addition, macrophages can degrade molecules inhibitory to axonal regeneration (Bedi et al., 1992) as well as release factors, such as interleukin-1 (IL-1), which can promote axonal growth via the induction of neurotrophic factors such as nerve growth factor (NGF) (Lindholm et al., 1987).

The precise mechanisms responsible for macrophage recruitment during WD are not completely understood. One group of factors that may play a role in macrophage recruitment and activation is the serum complement proteins. The importance of complement proteins immune-mediated peripheral nerve injury has been investigated previously.

Mead et al. (2002) showed that C6 deficient PVG/c rats, unable to form the membrane attack complex (MAC), exhibit neither demyelination nor axonal damage and significantly reduced clinical score in the antibody-mediated experimental autoimmune encephalomyelitis (EAE) model for multiple sclerosis when compared with matched C6 sufficient rats. However, levels of mononuclear cell infiltration were equivalent to those seen in C6 sufficient rats. Mead et al. (2002) concluded that demyelination and axonal damage occur in the presence of Ab and require activation of the entire complement cascade, including MAC deposition.

Jung et al. (1995) disclosed that treatment with recombinant human soluble complement receptor type 1 (sCR1) markedly suppressed clinical signs of myelin-induced experimental autoimmune neuritis (EAN) in Lewis rats (an animal model of the human Guillain-Barré syndrome). Extended demyelination and axonal degeneration were also prevented. These findings underscore the functional importance of complement during inflammatory demyelination in the peripheral nervous system.

Indeed, in EAN, complement depletion diminished myelin breakdown and macrophage recruitment in vivo (Feasby et al., 1987; Vriesendorp et al., 1995). Other groups have suggested that inhibition of the complement cascade reduces damage in neurodegenerative disease of the central nervous system (CNS) (e.g. Woodruff et al. 2006; Leinhase et al. 2006).

Daily et al. (1998) disclose a significant reduction in the recruitment of macrophages into distal degenerating nerve in complement-depleted animals. Complement depletion also decreased macrophage activation, as indicated by their failure to become large and multivacuolated and their reduced capacity to clear myelin. In the normal situation the myelin is cleared, the proximal part of the nerve forms sprouts which slowly grow along the path of the degenerated nerve. However, regeneration is slow (2-2.5 mm/day) and the environment of a degenerated nerve is full of factors which inhibit the growth of the axon and the necessary growth factors can be limiting or even absent. Myelin itself has been proposed to be a major inhibiting factor. Therefore rapid clearance of myelin is considered a conditio sine qua non for axonal regeneration. Thus the delayed clearance of myelin in complement-depleted animals is expected to result in impaired axonal regeneration. These findings indicate a role for serum complement in both the recruitment and activation of macrophages during peripheral nerve degeneration as well as an active role for macrophages in promoting axonal regeneration.

Indeed U.S. Pat. No. 6,267,955 discloses the methods wherein mononuclear phagocytes are administered at or near a site of injury or disease of the central or peripheral nervous system of a mammal in order to effect removal of the myelin debris that reportedly inhibits axonal regeneration, and for release of macrophage-derived cytokines that promote modulation of astrocytes and oligodendrocytes so as to support axonal regeneration.

Axonal degeneration is the main cause of disability both in hereditary and in acquired demyelinating neuropathies. While most current therapeutic research aims at restoring myelination, the present inventors focus on the consequence of demyelination: secondary axonal degeneration. As a model we have used acute demyelination and axonal degeneration after crush injury and subsequent regeneration of the nerve. It is an object of the present invention to provide for means and methods that promote and improve regeneration of nerves.

DESCRIPTION OF THE INVENTION

In the Examples herein we have observed activation of the complement (C)-system in the rat during WD and in human nerve biopsies of chronic demyelinating neuropathies. The present invention is based on the surprising finding that axonal regeneration is enhanced in rats that are deficient in the complement C6 factor. This surprising finding opens new ways to promote axonal regeneration by manipulation of the complement system and/or macrophage activation.

In a first aspect, therefore, the invention pertains to a method for treating a condition requiring axonal regeneration. The method comprises the administration of an inhibitor of a mammalian complement system, or the administration of a medicament (e.g. a pharmaceutical composition) comprising the inhibitor. Preferably an effective amount of the inhibitor is administered. Thus, in this aspect the invention pertains to an inhibitor of a mammalian complement system, or a medicament comprising the inhibitor, for use in a method for treating a condition requiring axonal regeneration. Similarly, in this aspect the invention pertains to the use of an inhibitor of a mammalian complement system for the manufacture of a medicament for the treatment of a condition requiring axonal regeneration. In the methods and uses of the invention the medicament preferably is a medicament for facilitation of axonal regeneration.

In the context of the present invention "facilitating axonal regeneration" is distinguished from reducing or preventing axonal degeneration. Facilitation (or promotion) of axonal regeneration is herein understood to mean that regeneration of an axon is improved in subjects that are treated as compared to non-treated subjects. Improved regeneration of an axon preferably is regeneration that occurs at an earlier point in time (after axonal injury or after start of the treatment) in treated subject as compared to non-treated subjects. Improved regeneration of an axon may also comprise regeneration that occurs at a higher rate and/or to a larger extent in treated subject as compared to non-treated subjects. A medicament according to the invention thus preferably produces a gain of sensory or motor function.

Improvement in axonal regeneration is preferably determined by functional tests that are relatively easily conducted in human subjects, e.g. recovery of sensory or motor function is preferably determined in a standardised test as is available in the art (see e.i. Wong et al., 2006; Jerosch-Herold, 2005). Suitable tests preferably are quantitative, standardised and more preferably have had their psychometric properties evaluated and quantified. Such tests include e.g. the Weinstein Enhanced Sensory Test (WEST) or the Semmes-Weinstein Monofilament Test (SWMT) and the shape-texture identification (STI) test for tactile gnosis. Improved axonal regeneration may experimentally be determined in test animals by functional tests for recovery of sensory or motor function as described by Hare et al. (1992) and De Koning et al. (1986). A medicament according to the invention thus preferably produces a gain of sensory or motor function, as may be determined in e.g. an above-indicated test.

Improved axonal regeneration may also be experimentally determined in test animals by histological examination. E.g. improved remyelination may be determined by comparing measurements of myelin sheaths around the axon in treated animals vs. non-treated animals, whereby a thicker myelin sheath is indicative of improved remyelination. More efficient axonal regeneration may be determined as the production of single, large diameter, axon sprouts in treated animals as compared to clusters of smaller axons in non-treated animals.

The appropriate dose of the inhibitor is that amount effective to promote axonal regeneration as may be seen by improvement of sensory or motor function as described above. By "effective amount," "therapeutic amount," or "effective dose" is meant that amount sufficient to elicit the desired pharmacological or therapeutic effects, thus resulting in effective treatment of the injury or disorder.

In order to minimise nerve injury and/or to facilitate axonal regeneration at soon as possible, in the methods of the invention, the medicament is preferably administered shortly after the occurrence of the nerve injury, i.e. within 24, 12, 6, 3, 2, or 1 hours, more preferably within 45, 30, 20 or 10 minutes after the occurrence of the nerve injury. In one embodiment of the invention, the medicament may be administered (e.g. as a precautionary measure) prior to surgery with a risk of nerve injury (see below), so as to minimise nerve injury and/or to facilitate axonal regeneration immediately upon surgical injury of the nerve.

Conditions Requiring Axonal Regeneration

A variety of conditions that require axonal regeneration may be treated with the methods and/or the medicaments of the invention. The conditions include injury of the PNS as well as injury of the CNS. The conditions include nerve trauma as a result of physical injuries as well as resulting from disease. Such diseases include immune-mediated inflammatory disorders or injuries and/or progressive neurodegenerative disorders which may be acquired and/or hereditary.

The physical injuries of the PNS and CNS may be traumatic injuries, including surgical injuries, or non-traumatic injuries. Traumatic PNS and CNS injuries that may be treated with the methods and/or the medicaments of the invention include spinal cord lesions as well as traumatic wounds to peripheral nerves, including injuries from collisions, motor vehicle accidents, gun wounds, fractures, dislocations, lacerations, or some other form of penetrating trauma. Peripheral nerves injured through trauma that may be treated include the digital, median, ulnar, radial, facial, spinal accessory and brachial plexus nerves.

Surgical PNS injuries are herein understood as injuries to peripheral nerves that arise when it becomes clinically necessary to remove or dissect a nerve during a surgical procedure. This occurs in thousands of surgical procedures each year. One example of surgically injured peripheral nerves that may be treated with the methods and/or medicaments of the invention include e.g. the cavernous nerves that support erectile function and bladder control; these nerves are often damaged during surgical removal of a prostate tumour and the tissue around it. Another example of a surgically injured peripheral nerve that may be treated in accordance with the invention is the phrenic nerve after coronary artery bypass grafting (CABG).

Non-traumatic physical PNS injuries that may be treated with the methods and/or the medicaments of the invention include compression and/or adhesion of peripheral nerves, also known as entrapment syndromes. The most common entrapment syndrome is carpal tunnel syndrome.

In addition immune-mediated inflammatory disorders or injuries may be treated with the methods and/or the medicaments of the invention. These include demyelinating diseases of the central and peripheral nervous systems that are believed to have an autoimmune basis and result in nerve demyelination as a result of damage caused to oligodendrocytes or to myelin directly. Such demyelinating diseases include e.g. Guillain-Barré syndrome (GBS; also referred to as inflammatory demyelinating polyneuropathy, acute idiopathic polyradiculoneuritis, acute idiopathic polyneuritis, French Polio and Landry's ascending paralysis). Preferably, methods and/or the medicaments of the invention are applied to promote axonal regeneration subsequent to acute phase in GBS. Similarly chronic inflammatory demyelinating polyneuropathy (CIDP), considered the chronic counterpart of GBS, may be treated with the methods and/or the medicaments of the invention.

Multiple sclerosis (MS) is another demyelinating disease that may be treated with the methods and/or the medicaments of the invention.

Further neurodegenerative CNS and/or PNS disorders with a genetic component that may be treated with the methods and/or the medicaments of the invention include Amyotrophic Lateral Sclerosis (ALS, sometimes called Lou Gehrig's disease), Charcot-Marie-Tooth disease (Hereditary Motor and Sensory Neuropathy, HMSN) and Huntington Disease (HD).

The Complement System

The complement system (see McAleer and Sim, 1993; Reid and Law, 1988) is concerned with host defence against infection. Upon activation of the system a catalytic set of reactions and interactions occur resulting in the targeting of the activating cell, organism or particle for destruction. The complement system comprises a set of over 30 plasma and membrane proteins that act together in a regulated cascade system to attack extra cellular forms of pathogens (e.g., bacterium). The complement system includes two distinct enzymatic activation cascades, the classical and alternative pathways which converge in a common terminal non-enzymatic pathway known as the membrane attack pathway.

The first enzymatically activated cascade, known as the classical pathway, comprises several components, C1, C4, C2, C3 and C5 (listed by order in the pathway). Initiation of the classical pathway of the complement system occurs following binding and activation of the first complement component (C1) by both immune and non-immune activators. C1 comprises a calcium-dependent complex of components C1q, C1r and C1s, and is activated through binding of the C1q component. C1q contains six identical subunits and each subunit comprises three chains (the A, B and C chains). Each chain has a globular head region that is connected to a collagen-like tail. Binding and activation of C1q by antigen-antibody complexes occurs through the C1q head group region. Numerous non-antibody C1q activators, including proteins, lipids and nucleic acids, bind and activate C1q through a distinct site on the collagen-like stalk region. The C1qrs complex then catalyzes the activation of complement components C4 and C2, forming the C4b2a complex which functions as a C3 convertase.

The second enzymatically activated cascade, known as the alternative pathway, is a rapid, antibody-independent route for complement system activation and amplification. The alternative pathway comprises several components, C3, Factor B, and Factor D (listed by order in the pathway). Activation of the alternative pathway occurs when C3b, a proteolytically cleaved form of C3, is bound to an activating surface agent such as a bacterium. Factor B is then bound to C3b, and cleaved by Factor D to yield the active enzyme, Ba. The enzyme Ba then cleaves more C3 to generate more C3b, producing extensive deposition of C3b-Ba complexes on the activating surface.

Thus, both the classical and alternate complement pathways produce C3 convertases that split factor C3 into C3a and C3b. At this point, both C3 convertases further assemble into C5 convertases (C4b2a3b and C3b3bBb). These complexes subsequently cleave complement component C5 into two components: the C5a polypeptide (9 kDa) and the C5b polypeptide (170 kDa). The C5a polypeptide binds to a 7 transmembrane G-protein coupled receptor, which was originally associated with leukocytes and is now known to be expressed on a variety of tissues including hepatocytes and neurons. The C5a molecule is the primary chemotactic component of the human complement system and can trigger a variety of biological responses including leukocyte chemotaxis, smooth muscle contraction, activation of intracellular signal transduction pathways, neutrophil-endothelial adhesion, cytokine and lipid mediator release and oxidant formation.

The larger C5b fragment binds sequentially to later components of the complement cascade, C6, C7, C8 and C9 to form the C5b-9 membrane attack complex ("MAC"). The lipophylic C5b-9 MAC can directly lyse erythrocytes, and in greater quantities it is lytic for leukocytes and damaging to tissues such as muscle, epithelial and endothelial cells. In sublytic amounts, the C5b-9 MAC can stimulate upregulation of adhesion molecules, intracellular calcium increase and cytokine release. In addition, at sublytic concentrations the C5b-9 MAC can stimulate cells such as endothelial cells and platelets without causing cell lysis. The non-lytic effects of C5a and the C5b-9 MAC are comparable and interchangeable.

Although the complement system has an important role in the maintenance of health, it has the potential to cause or contribute to disease.

Inhibitors of the Complement System

An inhibitor of a mammalian complement system for use in the methods and/or medicaments of the present invention may be an antagonist, polypeptide, peptide, antibody, antisense oligonucleotide, aptamer, miRNA, ribozyme, siRNA, or small molecule. The inhibitor preferably inhibits or blocks the formation of the membrane attack complex. The inhibitor preferably blocks activation of the complement system through both the classical and alternative pathway of complement. A preferred inhibitor is an inhibitor that blocks C3 convertase and MAC assembly. A further preferred inhibitor is an inhibitor that blocks one or more of C5, C6, C7, C8 and C9. The following compounds may thus be used in the methods and/or medicaments of the invention.

A preferred complement inhibitor for use in the present invention is a complement regulator, complement receptor or derivatives thereof. These include all natural regulators of the complement system such as C1-inhibitor, CR1, DAF, MCP, and CD59. Further included are derivatives of natural regulators of the complement system containing common structural units (CSR). CR1, MCP, DAF, C4 bp, fH all contain short consensus repeats (SCR). The SCR is a structural motif of 60-70 amino acids that is tandemly repeated 30 times in the F-allotype of CR1; the number of repeats can vary between allotypes. The consensus sequence of the SCR includes 4 cysteines, a glycine and a tryptophan that are invariant among all SCR. Sixteen other positions are conserved, with the same amino acid or a conservative replacement being found in over half of the 30 SCRs (Klickstein, et al., 1987, 1988; Hourcade, et al., 1988). Preferably the complement regulator containing SCRs comprises at least 3, 6, 12, 25 or 30 SCRs. Preferably the complement regulator containing SCRs is a soluble derivative of a complement receptor. Suitable examples thereof include e.g. sCR1 (TP10) which contains 30 SCRs, sMCP, sDAF, and CAB-2, which is a DAF/MCP hybrid. Modifications of these molecules allow targeting to membranes.

Soluble CR1 is a preferred inhibitor of complement activation because only CR1 combines specificity for both C3b and C4b with capabilities for dissociating the C3 convertases of both pathways and for cofactor activity in the proteolytic inactivation of C3b and C4b by factor I. In addition, these functions of CR1 are not restricted by alternative pathway activating functions, making the receptor suitable for suppressing activation by non-immunologic stimuli and inhibition of both classical and alternative pathway complement activation. Soluble CR1 (sCR1) fragments have been prepared by recombinant DNA techniques, using cDNA lacking the transmembrane and cytoplasmic domains (WO 89/09220; WO 91/05047). Preferred sCR1 molecules for use in the methods and/or medicaments of the invention are 1) a soluble CR1 protein that has the characteristics of the protein expressed by a Chinese hamster ovary cell DUX B11 carrying plasmid pBSCR1/pTCSgpt as deposited with the ATCC and assigned accession number CRL 10052; or 2) soluble complement receptor 1 TP10 (Avant Immunotherapeutics, Inc.).

A further complement regulator for use in the methods and/or medicaments of the invention is C1-inhibitor (C1INH). C1INH is a member of the serin protease inhibitor (serpins) family and it binds to the active site on both C1r and C1s inhibiting formation of the C1 complex. An advantage of plasma derived C1INH is its a long serum half-life (70 hours) in humans. Alternatively transgenic human C1INH may be used (WO 01/57079).

Yet another membrane-bound complement receptor for use in the methods and/or medicaments of the invention is Crry-Ig (Quigg et al., 1998). Crry is a membrane complement inhibitor with decay accelerating activity at the 3 convertase level, inhibiting both the classical and alternative pathway of complement. It also possesses cofactor activity comparable to that of CR1 for the factor I-mediated cleavage of C3b and C4b. Crry-Ig is a recombinant, soluble protein with an increased half-life (40 hours) due to fusion of Crry with the Fc portion of a non-complement-activating mouse IgG1 partner. Overall, Crry-Ig is potent complement inhibitor.

Antibodies or antibody-fragments against complement components are a further class of compounds that are of use in the methods and/or medicaments of the invention. In principle antibodies against any complement factor may be of use. However, preferred antibodies are antibodies that block C3 convertase and/or MAC assembly. A further preferred antibody is an antibody that blocks one or more of C5, C6, C7, C8 and C9. Preferably the antibody or fragment thereof is a monoclonal antibody (MAb). MAbs to complement components can be prepared using a wide variety of techniques known in the art including the use of hybridoma, recombinant, and phage display technologies, or a combination thereof. For example, monoclonal antibodies can be produced using hybridoma techniques including those known in the art and taught (i.e. Harlow et al., 1998; Hammerling, et al., 1981).

For treating humans, the anti-complement MAbs would preferably be used as chimeric, deimmunised, humanised or human antibodies. Such antibodies can reduce immunogenicity and thus avoid human anti-mouse antibody (HAMA) response. It is preferable that the antibody be IgG4, IgG2, or other genetically mutated IgG or IgM which does not augment antibody-dependent cellular cytotoxicity (Canfield and Morrison, 1991) and complement mediated cytolysis (Xu et al., 1994; Pulito et al., 1996). Chimeric antibodies are produced by recombinant processes well known in the art, and have an animal variable region and a human constant region. Humanised antibodies have a greater degree of human peptide sequences than do chimeric antibodies. In a humanised antibody, only the complementarity determining regions (CDRs) which are responsible for antigen binding and specificity are animal derived and have an amino acid sequence corresponding to the animal antibody, and substantially all of the remaining portions of the molecule (except, in some cases, small portions of the framework regions within the variable region) are human derived and correspond in amino acid sequence to a human antibody. See Riechmann et al., 1988; Winter, U.S. Pat. No. 5,225,539; Queen et al., U.S. Pat. No. 5,530,101. Deimmunised antibodies are antibodies in which the T and B cell epitopes have been eliminated, as described in WO9852976. They have reduced immunogenicity when applied in vivo.

Human antibodies can be made by several different ways, including by use of human immunoglobulin expression libraries (Stratagene Corp., La Jolla, Calif.) to produce fragments of human antibodies (VH, VL, Fv, Fd, Fab, or (Fab')2, and using these fragments to construct whole human antibodies using techniques similar to those for producing chimeric antibodies. Human antibodies can also be produced in transgenic mice with a human immunoglobulin genome. Such mice are available from Abgenix, Inc., Fremont, Calif., and Medarex, Inc., Annandale, N.J.

One can also create single peptide chain binding molecules in which the heavy and light chain Fv regions are connected. Single chain antibodies ("ScFv") and the method of their construction are described in U.S. Pat. No. 4,946,778. Alternatively, Fab can be constructed and expressed by similar means (Evans et al., 1995).

Another class of antibodies that may be used in the context of the present invention are heavy chain antibodies and derivatives thereof. Such single-chain heavy chain antibodies naturally occur in e.g. Camelidae and their isolated variable domains are generally referred to as "VHH domains" or "nanobodies". Methods for obtaining heavy chain antibodies and the variable domains are inter alia provided in the following references: WO 94/04678, WO 95/04079, WO 96/34103, WO 94/25591, WO 99/37681, WO 00/40968, WO 00/43507, WO 00/65057, WO 01/40310, WO 01/44301, EP 1134231, WO 02/48193, WO 97/49805, WO 01/21817, WO 03/035694, WO 03/054016, WO 03/055527, WO 03/050531, WO 01/90190, WO 03/025020, WO 04/041867, WO 04/041862, WO04/041865, WO 04/041863, WO 04/062551.

All of the wholly and partially human antibodies are less immunogenic than wholly murine MAbs, and the fragments and single chain antibodies are also less immunogenic. All these types of antibodies are therefore less likely to evoke an immune or allergic response. Consequently, they are better suited for in vivo administration in humans than wholly animal antibodies, especially when repeated or long-term administration is necessary. In addition, the smaller size of the antibody fragment may help improve tissue bioavailability, which may be critical for better dose accumulation in acute disease indications, such as tumour treatment.

Suitable anti-complement antibodies are already available. E.g. the anti-C5 MAb produced by hybridoma 5G1.1 having ATCC designation HB-11625 (N19-8) as described in U.S. Pat. No. 6,355,245; anti-C3a MAb from Quidel, San Diego, Calif. [catalog no. A203,]; anti-human C3aR antibodies hC3aRZ1 and hC3aRz2, as described in Kacani et al., (2001); mouse anti-human C5a antibodies from Hycult Biotechnology BV of the Netherlands [clones 557, 2942 and 2952]; anti-human C5a antibody from Tanox, Inc. [137-26], as described in Fung et al. (2003); C5a antibodies disclosed in U.S. Pat. No. 5,480,974; anti-EX1 human C5aR MAb S5/1, as described in Oppermann et al., (1993); anti-C5aR MAb S5/1, as described in Kacani et al., (2001); and anti-05a MAb as described in U.S. Pat. No. 5,177,190.

A further compound that may be used in the methods and/or medicaments of the invention is cobra venom factor (CVF) or a derivative thereof that depletes C3 by binding Factor B and formation of a C3 convertase activity that is resistant to natural fluid phase regulators. A preferred CVF derivative is e.g. a derivative that can be targeted to the site of injury.

Other useful compounds include poly-anionic inhibitors of complement such as heparin, N-acetylated heparin and suramin. Heparin inhibits C by binding to C1, blocking C3 convertase and MAC assembly. N-acetylated heparin has a reduced anticoagulant activity.

In addition a variety of synthetic and/or natural small molecules that inhibit complement may be used in the methods and/or medicaments of the invention, e.g. the natural inhibitors K-76COOH (derived from *Stachybotrys complementi*), which inhibits C5, and rosmaric acid derived from Rosemary, which binds and inhibits C3b and thereby prevents convertase formation, synthetic protease inhibitors such as e.g. nafamastat mesilate (FUT-175), which binds C1r, C1s, Factor D and C3/C5 convertase, inhibitors of the C1 complex such e.g. C1s-INH-248 and BCX-1470 (already tested in humans for safety), peptide inhibitors such as molecules containing parts of or derived from complement binding natural molecules, such as e.g. derivatives containing the carboxyterminal part of serpins, compstatin (a 13 a.a. cyclic molecule that binds C3), and the C5 receptor agonists PMX53 and PMX205.

Methods for producing nucleic acid inhibitors of complement such as anti-sense oligonucleotide, aptamer, miRNA, ribozyme, siRNA, are known to the skilled person persé. Preferably such nucleic acid inhibitors comprise one or more modified nucleotides such as e.g. 2'-O substituted ribonucleotides, including alkyl and methoxy ethyl substitutions, peptide nucleic acid (PNA), locked nucleic acid (LNA) and morpholino antisense oligonucleotides and ethylene-bridged nucleotides (ENA) and combinations thereof.

In the above methods of the invention, the compounds may be administered by any convenient route, for example by infusion or bolus injection. Various delivery systems are known and can be used for delivery of the inhibitor compounds. These include encapsulation in liposomes, microparticles, or microcapsules. Although in the methods of the invention administration of the compounds by oral and/or mucosal routes (intranasal, inhalation, rectal) is not excluded, usually the complement inhibitors will be administered parenterally, including e.g. intradermal, intramuscular, intraperitoneal, intravenous, and subcutaneous routes. The compounds may be administered systemically or may be used by local, topical or regional administration at or near a site of disease or injury, e.g. using injection and/or any neurosurgically suitable technique.

The invention further relates to a pharmaceutical preparation comprising as active ingredient a complement inhibitor as defined above. The composition preferably at least comprises a pharmaceutically acceptable carrier in addition to the active ingredient. The pharmaceutical carrier can be any compatible, non-toxic substance suitable to deliver the inhibitors to the patient. Sterile water, alcohol, fats, waxes, and inert solids may be used as the carrier. Pharmaceutically acceptable adjuvants, buffering agents, dispersing agents, and the like, may also be incorporated into the pharmaceutical compositions.

For oral administration, the inhibitor can be administered in solid dosage forms, such as capsules, tablets, and powders, or in liquid dosage forms, such as elixirs, syrups, and suspensions. Active component(s) can be encapsulated in gelatine capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain colouring and flavouring to increase patient acceptance.

The inhibitors are however preferably administered parentally. Suitable carriers for parental formulations include saline, buffered saline, dextrose, and water. Typically compositions for parenteral administration are solutions in sterile isotonic aqueous buffer. Sterilisation is readily accomplished by filtration through sterile filtration membranes, prior to or following lyophilisation and reconstitution. A typical composition for intravenous infusion could be made up to contain 10 to 50 ml of sterile 0.9% NaCl or 5% glucose optionally supplemented with a 20% albumin solution and an appropriate amount (1 to 1000 μg) of the inhibitor. A typical pharmaceutical composition for intramuscular injection would be made up to contain, for example, 1-10 ml of sterile buffered water and 1 to 1000 μg of the of the inhibitor. Methods for preparing parenterally administrable compositions are well known in the art and described in more detail in various sources, including, for example, Remington's Pharmaceutical Science (15th ed., Mack Publishing, Easton, Pa., 1980) (incorporated by reference in its entirety for all purposes). Where necessary, the composition may also include a solubilising agent and a local anaesthetic such as lignocaine to ease pain at the site of the injection. Generally, the ingredients will be supplied either separately or mixed together in unit dosage form, contained in a hermetically sealed container such as an ampoule or sachette indicating the quantity of active agent in activity units. Where the composition is to be administered by infusion, it can be dispensed with an infusion bottle containing sterile pharmaceutical grade 'Water for Injection' or saline. Where the composition is to be administered by injection, an ampoule of sterile water for injection or saline may be provided so that the ingredients may be mixed prior to administration.

In those methods where the inhibitor is a polypeptide or antibody it may be purified from mammalian, insect or microbial cell cultures, from milk of transgenic mammals or other source and be administered in purified form together with a pharmaceutical carrier as a pharmaceutical composition. Methods of producing pharmaceutical compositions comprising polypeptides are described in U.S. Pat. Nos. 5,789,543 and 6,207,718. The preferred form depends on the intended mode of administration and therapeutic application. The concentration of the polypeptides or antibodies of the invention in the pharmaceutical composition can vary widely, i.e., from less than about 0.1% by weight, usually being at least about 1% by weight to as much as 20% by weight or more.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

EXAMPLES

1. Example 1

Improved Post-Traumatic Nerve Recovery in Complement Component C6 Deficient Rats as Compared to Wild-Type Rats 1.1 Electron Microscopic Analysis We have explored the role of the complement system in acute and chronic nerve injury and during regeneration. As a model we used the complement C6 deficient PVG rat strain (Bhole and Stahl, 2004) and compared this with wild type PVG rats. Since the complement system has many functions we chose an animal model in which only the most terminal effectors of the complement cascade was defective.

The effect of complement inhibition on nerve regeneration was studied in the acute model of nerve crush (Glass, 2004).

Figure 1:
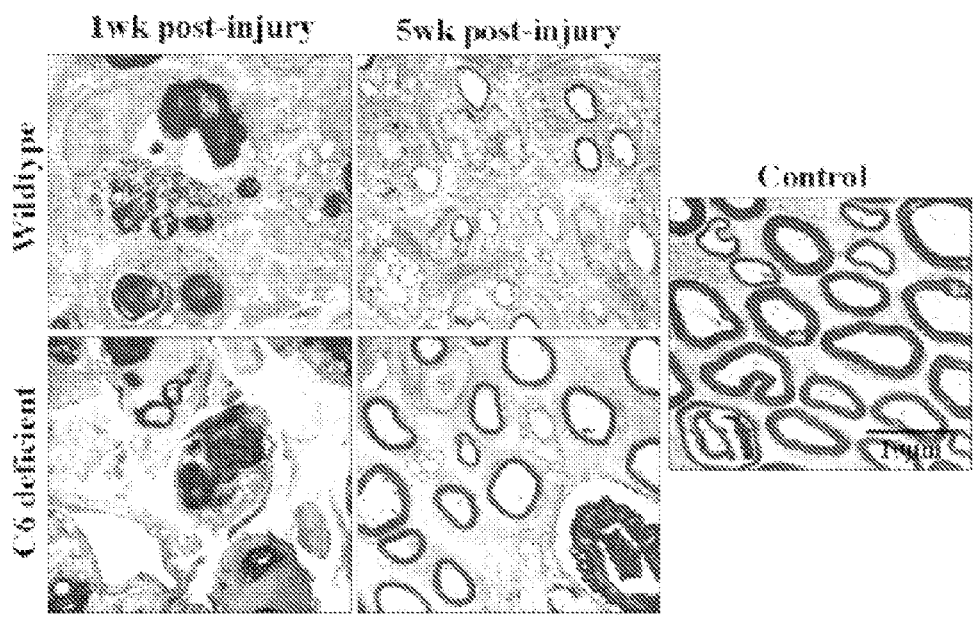
FIG. 1. The effect of complement C6-deficiency on regeneration of the tibial nerve. The right sciatic nerve was crushed for 30 seconds in wild type and C6-deficient PVG rats. Tibial nerve was analyzed 1 and 5 weeks after injury. Control picture: left tibial nerve of a PVG rat.

The right sciatic nerve was crushed for 30 seconds in wild type as well as in the C6-deficient PVG rats. Tibial nerve was then analyzed 1 and 5 weeks after injury (see FIG. 1).

At one week, electron microscopy shows equally severe degeneration in wild type and in C6 deficient rats. At 5 weeks, the C6 deficient rats already show myelinated axons, whereas the wild type rats exhibit incipient recovery. In the C6 deficient animals most myelinated axons show the normal one to one ratio with Schwann cells (compare with the control picture of the left tibial nerve of a PVG rat). In contrast, in the wild type rats there are several myelinated fibres in each regenerative cluster.

We found two effects of C6 deficiency on post-traumatic nerve recovery:

1) The clearance of myelin during Wallerian degeneration was delayed in the C6 deficient animals. Wild type rats showed signs of WD (myelin degeneration, macrophage activation) already after 24 hours. In C6-deficient animals this process was delayed. Only after 72 hrs myelin degeneration was visible and macrophage activation did not occur. After one week both types of animals showed severe nerve degeneration.

2) Unexpectedly however, the post-traumatic nerve recovery was much better in complement component C6 deficient rats compared to wild-type rat. Remyelination of single axons occurred much faster in the C6 deficient animals and the sprouting process was more efficient since a single, large diameter, axon sprout was produced rather than a cluster of smaller axons. See FIG. 1.

1.2 C6 Deficiency Leads to a Delayed Influx/Activation of Phagocytic Cells

In view of the important role of macrophages in myelin clearance, we next analyzed the number and activation state of macrophages after crush.

ED1 (CD68) immunoreactive (-ir) cells were counted in non-consecutive sections of crushed sciatic nerves at 0, 24, 48 and 72 hr post-injury that were taken from wild type rats, C6 deficient rats and C6 deficient rats that were supplemented with C6, respectively.

Figure 2:
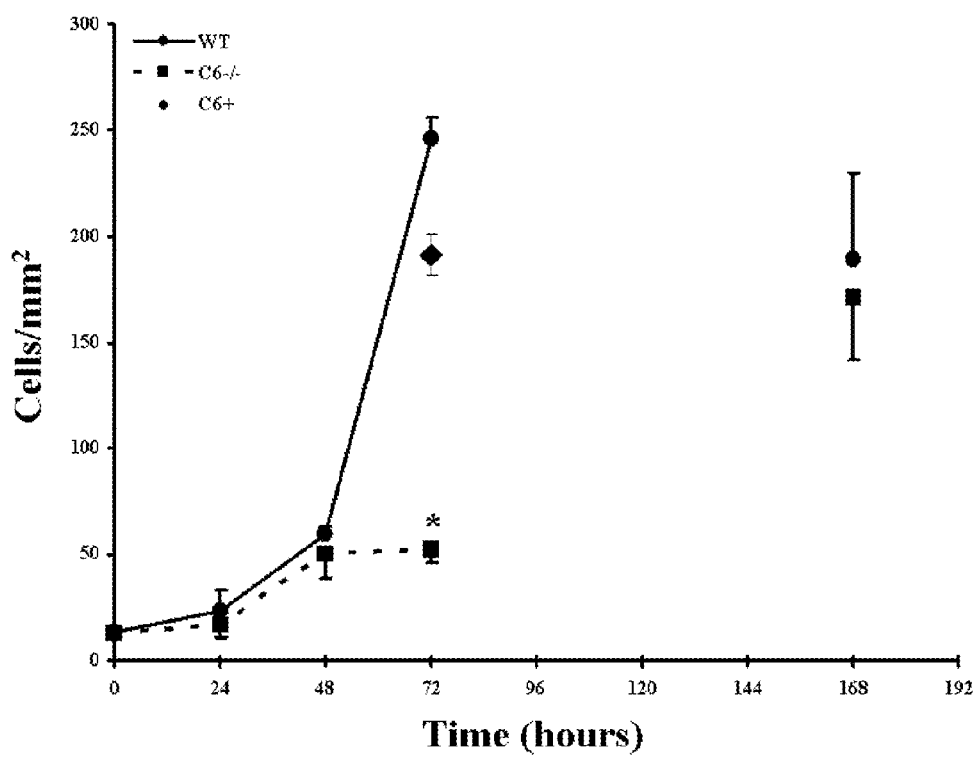
FIG. 2. C6 deficiency leads to a delayed influx/activation of phagocytic cells. ED1 (CD68) immunoreactive (-ir) cells were counted in non-consecutive sections of sciatic nerves from WT (wild type), C6−/− (C6-deficient) and C6+ (C6-deficient rats supplemented with C6) rats at 0, 24, 48 and 72 h post-injury. Statistical significance indicated by the asterisk (*) refers to $p<0.05$.

In both the wild type and C6 deficient animals, CD68 (ED1 antibody) positive cells accumulated in the crushed nerve. However, the C6 deficient animals showed a delayed appearance of CD68 positive cells (FIG. 2, compare solid and dotted line). C6 suppletion restored the accumulation of CD68 cells (see 72 hr time point). In the C6 deficient animals there was a lack of activation of macrophages, as assayed by immunohistochemistry CR3 (ED7 antibody) staining (not shown).

Since lymphnodes of these animals contain CR3 positive cells we could exclude that the C6 deficient animals are defective in macrophage activation per se. In addition, upon C6 reconstitution, the accumulation of CD68 positive cells and CR3 expression on macrophages was restored and subsequently myelin degeneration occurred. This directly links steps in the complement pathway downstream of C6, i.e. Membrane Attack Complex (MAC) formation to WD.

After 7 days equal number of CD68 positive cells were found in the C6 deficient and wild type cells. These cells do not display ED7 (CR3) in the C6 deficient animals and are most likely not activated macrophages (data not shown).

Figure 3:
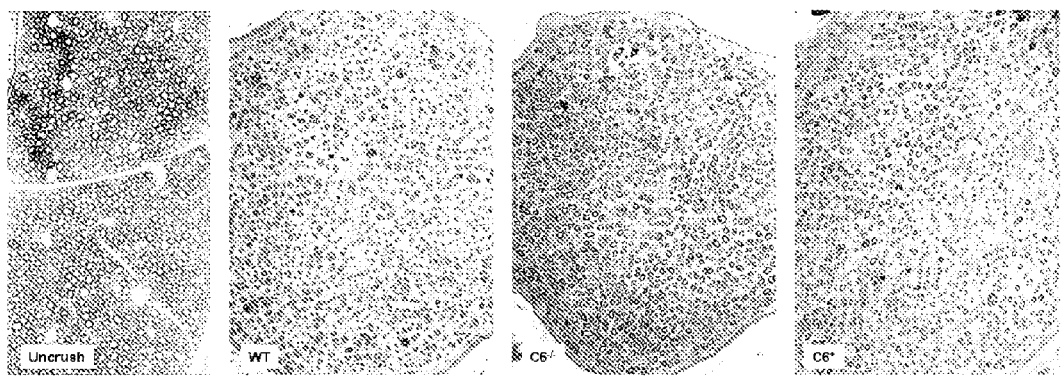
FIG. 3. The effect of C6 reconstitution on regeneration. Analysis of myelinated axons during regeneration. Light microscopy on semi-thin sections of the proximal site of the rat tibial nerve at 5 wk post-injury. From left to right: uncrushed nerve; wild type nerve (WT); C6-deficient nerve (C6−/−); and, C6-deficient nerve reconstituted with C6 (C6+).

1.3 Neuropathological and Functional Assays of C6 Deficiency and Reconstitution FIG. 3 shows light microscopic analysis of myelinated axons during regeneration. Semi-thin sections of the proximal site of the rat tibial nerve were analysed at 5 weeks post-injury of wild type rats, C6 deficient rats and C6 deficient rats reconstituted with C6. Few thinly myelinated axons are present in the wild type (WT) nerve while many thickly myelinated axons are present in the C6 deficient (C6−/−) nerve. The nerve from the rat that was reconstituted with C6 (C6+) shows less myelinated axons than the C6 deficient nerve.

Figure 4:
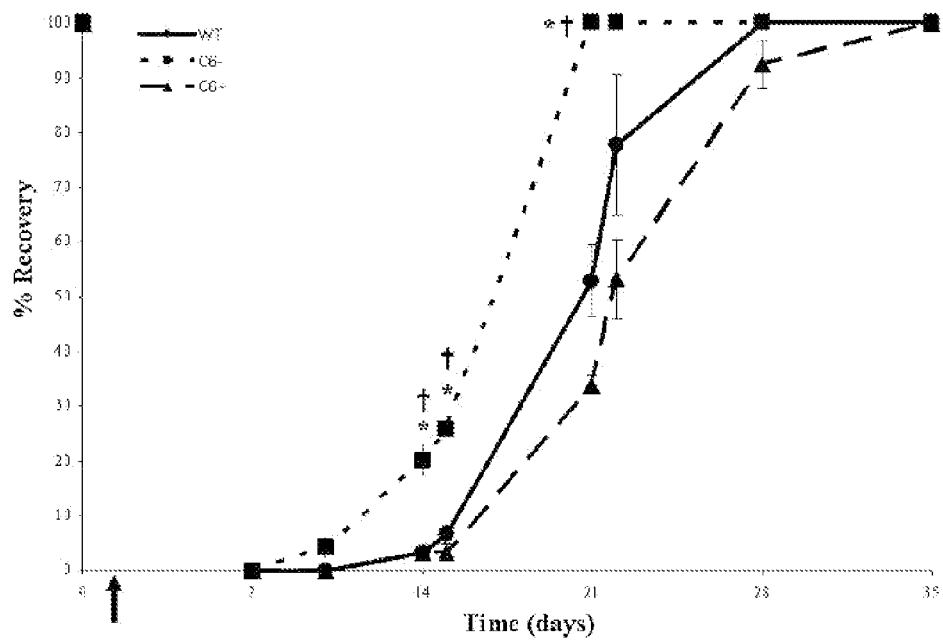
FIG. 4. The effect of C6 reconstitution on functional recovery. Recovery of sensory function as measured with the footflick apparatus at currents ranging from 0.1 mA to 0.5 mA. Values are normalised to control levels. The arrow (→) indicates the time at which the crush injury was performed. WT=wild type rats; C6−/−=C6-deficient rats; and, C6+=C6 reconstitution in C6-deficient animals. Statistical significance between C6−/− and WT (*) or C6+ (†) is for $p<0.05$.

FIG. 4 shows the effect of C6 reconstitution on functional recovery of the nerve. Recovery of sensory function was measured with the footflick apparatus at currents ranging from 0.1 mA to 0.5 mA. Values were normalised to control levels. The arrow (→) indicates the time at which the crush injury was performed. Wild type rats take 4 weeks to fully recover while C6 deficient rats are already recovered at 3 weeks post-crush. C6 reconstitution in C6 deficient animals results in the wild type (slow) regeneration phenotype after crush. Statistical significance between C6−/− and WT (*) or C6+ (†) is for $p<0.05$.

We conclude that the observed effect on regeneration of the PNS after crush is due to the C6 deficiency since reconstitution of the C6 deficient rats with purified human C6 restores the wild type phenotype in neuropathological and functional assays (FIGS. 3 and 4).

Example 2

Inhibition of Complement Activation after Nerve Crush by Human C1-Inhibitor

Figure 5:
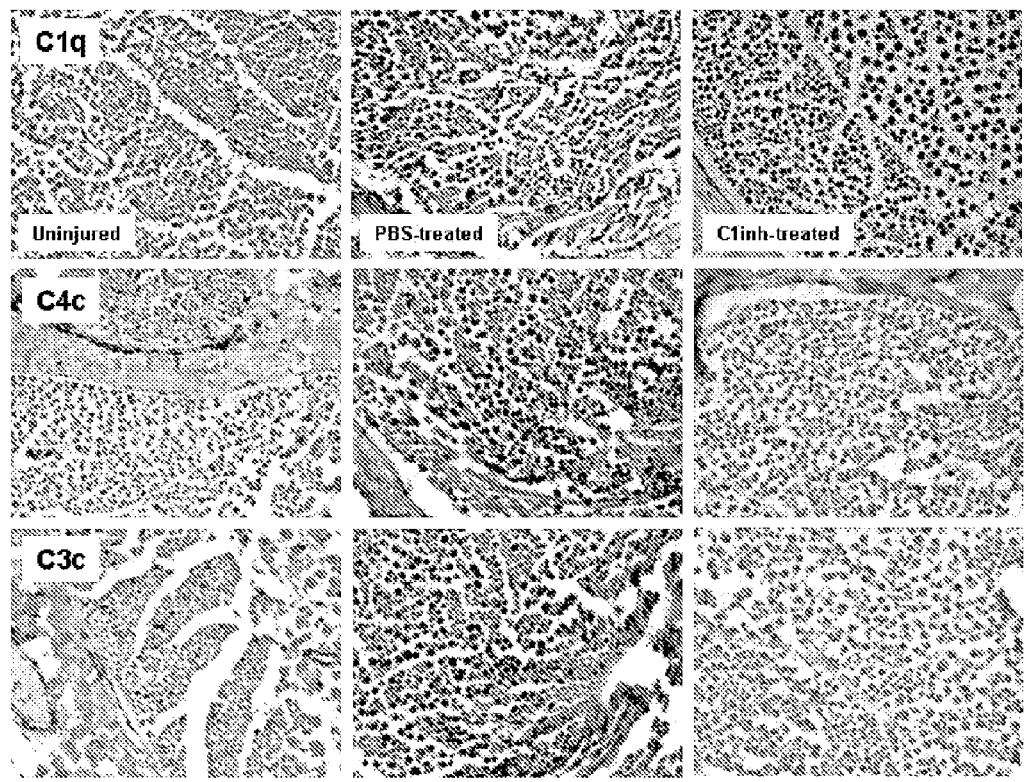
FIG. 5. Recombinant human C1-inhibitor (rhC1INH) inhibits complement activation after crush. C1q, C4c and C3c immunostaining of injured wild type rat sciatic nerves treated with rhC1INH or vehicle (PBS) alone.

We tested whether recombinant human C1-inhibitor (rhC1INH; obtained from Pharming, Leiden, The Netherlands) is able to inhibit the rapid (1 hr) complement activation after nerve crush. FIG. 5 shows C1q, C4c and C3c immunostaining of injured wild type rat sciatic nerves treated with rhC1INH or vehicle (PBS) alone at 1 hour after nerve crush. High immunoreactivity for C1q is present in all crushed nerves, confirming C1q up-regulation after the crush injury. C4c and C3c immunoreactivity was detected in the PBS-treated nerves as expected but no C4c and C3c immunoreactivity was detected in the nerves from the rhC1INH treated rats sacrificed at 1 hr post-injury. This demonstrates effective blockade of the complement cascade by rhC1INH after crush and suggests that the alternative pathway of complement activation is not involved in the crush injury model of Wallerian degeneration. Thus, activation of the complement cascade after nerve crush occurs through the classical pathway. There is one caveat however: due to the short half life of rhC1INH in rats, we could only monitor C3 and C4 cleavage 1 hr after crush. Therefore we cannot exclude that activation through the alternative pathway occurs at a later time point.

Example 3

The Effect of Soluble CR1 on Post Traumatic Nerve Regeneration

Next, we tested the effect of soluble CR1 (sCR1) on post traumatic nerve regeneration. sCR1 inhibits the C3/C5 convertase, and thereby affects both the classical and alternative pathway of the complement system.

Wild type PVG rats were treated with soluble CR1 (TP10 from Avant Immunotherapeutics, Inc.) at a dose of 15 mg/kg/day (TP10 soluble CR1 was obtained from Prof. P. Morgan, Cardiff, UK). Control rats were treated with the same volume (600 μl) of vehicle alone (PBS). Soluble CR1 or PBS was delivered i.p. 24 hours before the crush and every following day for a maximum of 8 injections (up to day 6 after crush). The sciatic nerve of the right leg was crushed and the left leg served as control. Both histology and sensory function were analysed.

Figure 6:
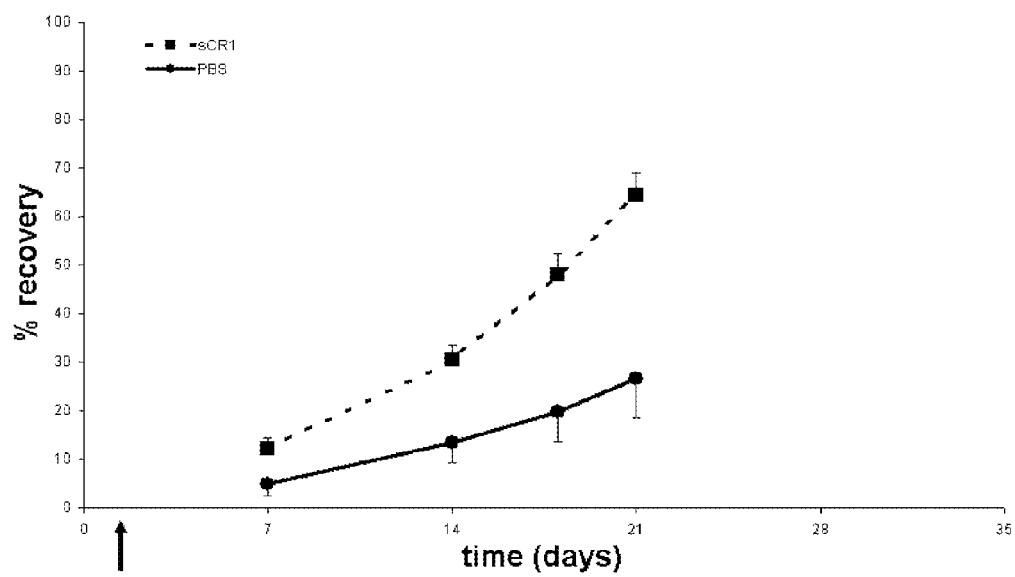
FIG. 6. The effect of soluble CR1 on post traumatic nerve regeneration. Recovery of sensory function as measured with the footflick apparatus at currents ranging from 0.1 mA to 0.5 mA. Values are normalised to control levels. The arrow (→) indicates the time at which the crush injury was performed. PBS=control with vehicle only; sCR1=soluble CR1.

FIG. 6 shows that in a functional analysis with the footflick test a faster recovery of the sensory function is seen in the sCR1-treated animals compared to the PBS-treated. The footflick test was performed as described above in Example 1.3.

Figure 7:
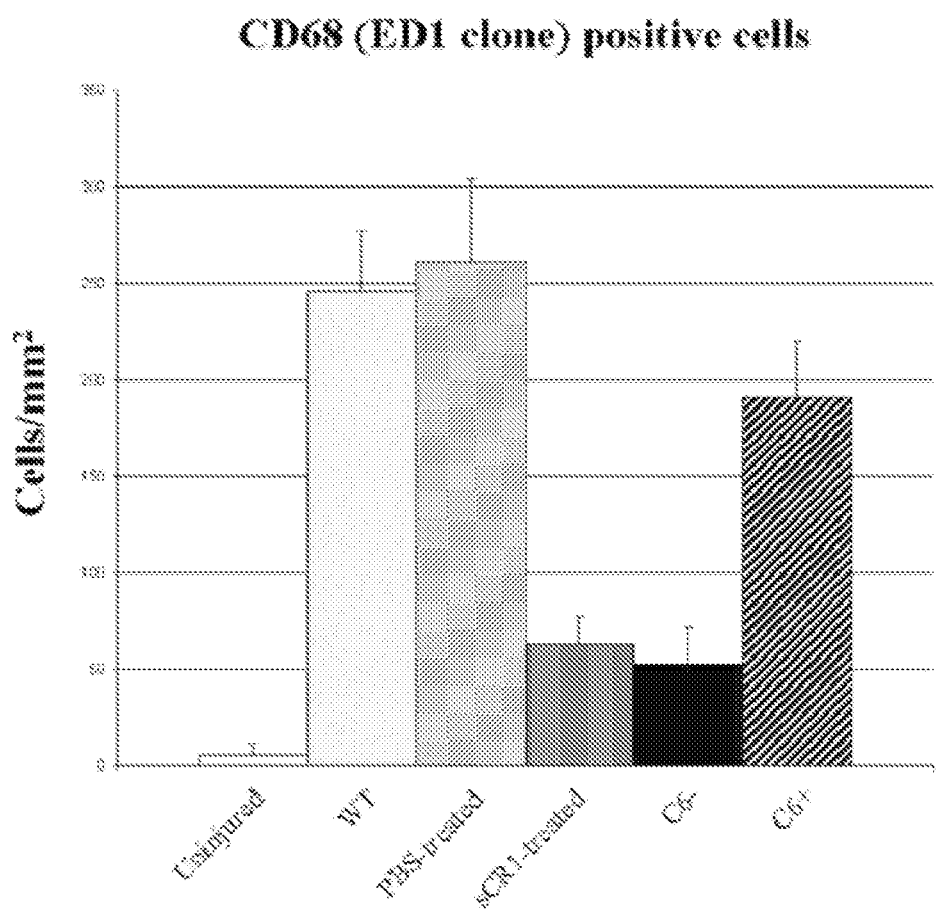
FIG. 7. Activation of macrophages after nerve crush is dependent on activation of a downstream component of the complement cascade. CD68 positive cells were determined by immunostaining with the ED1 antibody. In wild type (WT) and vehicle (PBS) treated animals the number of CD68 positive cells in the distal part of the lesioned sciatic nerve increased 72 hours after nerve crush. Treatment with sCR1 blocked this activation to a similar level as seen in C6 deficient rats (C6−). C6 reconstitution in the C6 deficient animals (C6+) resulted in almost complete recovery from this block in activation.

Histological analysis of nerves at 72 hrs after the crush shows that sCR1 strongly inhibited the influx and activation of macrophages (see FIG. 7). sCR1 treatment resulted in similar levels of inhibition of macrophage activation as measured by CD68 positivity as compared to deficiency of C6.

Example 4

Inhibition of Complement Activation Facilitates Axon Regeneration and Recovery in a Model of Peripheral Nerve Injury 4.1 Methods 4.1.1 Animals This study was approved by the Academic Medical Center Animal Ethics Committee and complies with the guidelines for the care of experimental animals. Male 12 weeks old PVG/c (wildtype) were obtained from Harlan (UK) and PVG/c$^-$ (C6$^{-/-}$) rats were bred in our facility. The animals weighed between 200 g and 250 g and were allowed to acclimatize for at least two weeks before the beginning of the study. Animals were kept in the same animal facility during the entire course of the experiment and monitored for microbiological status according to the FELASA recommendations. Animals were housed in pairs in plastic cages. They were given rat chow and water ad libitum and kept at a room temperature of 20° C. on a 12 hours:12 hours light:dark cycle.

4.1.2 Genotyping of PVG/c- (C6$^{-/-}$) Rats

The C6$^{-/-}$ rats carry a deletion of 31 basepairs (bp) in the C6 gene (Bhole and Stahl, 2004). Genotypaing was performed according to Ramaglia et al (2007).

4.1.3 Administration of Human C6 for Reconstitution Studies

C6 was purified from human serum (Mead et al., 2002). It was administered i.v. in eight C6$^{-/-}$ rats at a dose of 4 mg/kg/day in PBS one day before the crush injury (day −1) and every day thereafter for 1 week (day 0, 1, 2, 3, 4, 5, 6). Eight wildtype and eight C6$^{-/-}$ rats were treated with equal volume of vehicle (PBS) alone. The C6$^{-/-}$ rats reconstituted with purified human C6 will be indicated in the text as C6$^+$.

4.1.4 Administration of sCR1 for Inhibition Studies

Recombinant soluble complement receptor 1 (sCR1) was obtained as previously described (Piddlesden et al., 1994). sCR1 was administered i.p. in six rats at a dose of 15 mg/kg/day. Six rats were treated with equal volumes of vehicle (PBS) alone. The treatment was given one day before the crush injury (day −1) and every day thereafter for 1 week (day 0, 1, 2, 3, 4, 5, 6).

4.1.5 Hemolytic Assay and ELISA

Blood samples from wildtype PBS-treated, C6$^{-/-}$ PBS-treated, C6$^+$ and sCR1-treated rats were collected from the tail vein one day before the crush injury (day −1) and every following day until 1 week post-injury (day 0, 1, 2, 3, 4, 5, 6, 7). All samples were collected immediately before each injection of treatment. Plasma was separated and stored at −80° C. until used to monitor C6 activity and sCR1 inhibitory effect via standard complement hemolytic assay (Morgan, 2000). Plasma levels of sCR1 were measured using ELISA assay as previously described (Mulligan et al., 1992) using serial dilutions assayed in duplicates.

4.1.6 Motor and Sensory Test

All experiments were conducted by the same investigator who was blinded of the genotype and treatment groups. Both motor and sensory tests were performed at the same time during the day, every week until 5 weeks post-injury. Recovery of motor function was assessed using a standardized walking track analysis and derived sciatic functional index (SFI) according to Hare et al (1992). Briefly, the rats were allowed to walk across a plexiglas platform while their walking patter was recorded by a camera underneath the platform. An index of the sciatic nerve function was calculated from the recorded footprints using the ImagePro analysis program (Media Cybernatics, The Netherlands). The print length (PL), toe ($1^{st}$ to $5^{th}$) spread (TS) and intermediary toe ($2^{nd}$ to $4^{th}$) spread (IT) were recorded from the uninjured normal foot (NPL, NTS, NIT) and the contralateral foot on the injured experimental side (EPL, ETS, EIT). The SFI was derived with the formula: $-38.3*[(EPL-NPL)/NPL]+109.5*[(ETS-NTS)/NTS]+13.3*[(EIT-NIT)/NIT]$. In case on no print produced by the animals, the standard values of EPL=60 mm, ETS=6 mm and EIT=6 mm were used according to De Koning et al (1986). Recovery of sensory function was assessed with the footflick test according to De Koning et al (1986). Briefly, a shock source with a variable current of 0.1-0.5 mA was used. Recordings were performed one day before the injury and every week until 5 weeks post-injury. The rats were immobilized and two stimulation electrodes were placed at the same point on the rat foot sole for every animal and stimulation. A response was scored positive if the rat retracted its paw. The current (mA) at which the retraction occurred was recorded. Values are expressed as percentage of normal function.

4.1.7 Nerve Crush Injury

All the surgical procedures were performed aseptically under deep isoflurane anesthesia (2.5% vol isoflurane, 1 L/min O$_2$ and 1 L/min N$_2$O). The left thigh was shaved and the sciatic nerve was exposed via an incision in the upper thigh. The nerve was crushed for three 10 s periods at the level of the sciatic notch using smooth, curved forceps (No. 7). The crush site was marked by a suture which did not constrict the nerve. On the right side, sham surgery was performed which exposed the sciatic nerve but did not disturb it. A suture was also placed. The muscle and the skin were then closed with stitches. The right leg served as control. Following the crush, the rats were allowed to recover for 1 (wildtype n=5; C6$^{-/-}$ n=5; C6$^+$ n=2), 3 (wildtype n=6; C6$^{-/-}$ n=6; C6$^+$ n=3) and 5 (wildtype n=5; C6$^{-/-}$ n=5; C6$^+$ n=3; wildtype sCR1-treated n=6; wildtype PBS-treated n=6) weeks.

4.1.8 Tibial Nerve Histology

All animals were intracardially perfused with 4% paraformaldehyde in piparazine-N-N'-bis(2-ethane sulphonic acid) (PIPES) buffer (pH 7.6), under deep isoflurane anesthesia. Left and right tibial nerves were removed from each animal and postfixed with 1% glutaraldehyde, 1% paraformaldehyde and 1% dextran (MW 20,000) in 0.1 M PIPES buffer (pH 7.6). They were divided into one proximal and one distal segment of 10 mm length. Each segment was conventionally processed into epoxy resin. Semithin resin sections of 0.5 μm were stained with thionine and acridine orange and images were captured with a light microscope (Leica DM5000B, The Netherlands) connected to a digital camera (Leica DFC500, The Netherlands). Electron microscopy was performed on ultrathin sections of the tibial nerve from wildtype and C6 rats at 5 weeks following the crush injury. Sections were contrasted with uranyl acetate and lead citrate as previously described (King, 1999). Images were captured with a digital camera attached to an electron microscope (FEO 10, Philips, The Netherlands). The number of regenerative clusters of axons at 5 weeks post-injury was determined on semithin resin section. The entire section was scored per each animal in each group. The g-ratio is the numerical ratio of unmyelinated axon diameter to myelinated axon diameter and was calculated over the entire nerve section. The frequency of large caliber (>8 µm) myelinated fibers was calculated over the entire nerve section.

4.1.9 Statistical Analysis

Two way ANOVA with Bonferroni correction was performed to determine statistically significant differences in the hemolytic assay (p<0.001), ELISA assay (p<0.001), SFI (p≤0.05), Footflick test (p≤0.05).

4.2 Results and Discussion

To test the effects of C activation on nerve regeneration after acute trauma we determined the effect of C on recovery from crush injury of the sciatic nerve in the rat model in two complementary ways, first by examining the effects of C6 deficiency ($C6^{-/-}$) and second by inhibition of C activation.

The study was set up according to a scheme that extends over a period of 5 weeks. Time 0 is the time of the crush injury. Each group of animals was treated either with placebo (PBS) or purified C6 protein or sCR1 the day before the injury (day −1) and every day thereafter until 1 week post-injury. Blood was collected from each animal the day before the injury (day-1) and at days 0, 1, 2, 3, 5 and 7 post-injury to determine serum complement haemolytic activity. Functional analysis, to determine recovery of motor function by the sciatic functional index (SFI) and recovery of sensory function by the footflick test, was performed 1 day before the injury for baseline values and every week thereafter until 5 weeks post-injury. Pathological analysis of the tibial nerves distal from the site of injury was performed at weeks 1, 3 and 5 post-injury to determine nerve regeneration.

Both functional recovery and effects on histology were determined. As controls for C6 deficiency we reconstituted $C6^{-/-}$ rats with purified C6 protein (4 mg/kg/day; n=8) (C6+), which restored the plasma hemolytic activity ($CH_{50}$) to wildtype levels (>80%; p<0.001, two way ANOVA) (Table 1) Inhibition of C activation was achieved by systemic treatment with soluble C receptor 1 (sCR1) (15 mg/kg/day; n=6), a recombinant soluble form of the human membrane C regulator CR1 which inhibits all three C activation pathways (Weisman et al., 1990). This treatment reduced hemolytic C activity to about 30% of the PBS vehicle-treated controls (n=6; p<0.001, two way ANOVA) over the entire course of the treatment (Table 1). We found this level of C inhibition in the plasma completely abrogated deposition of activated C in the nerve at 3 days after injury.

Figure 8A:
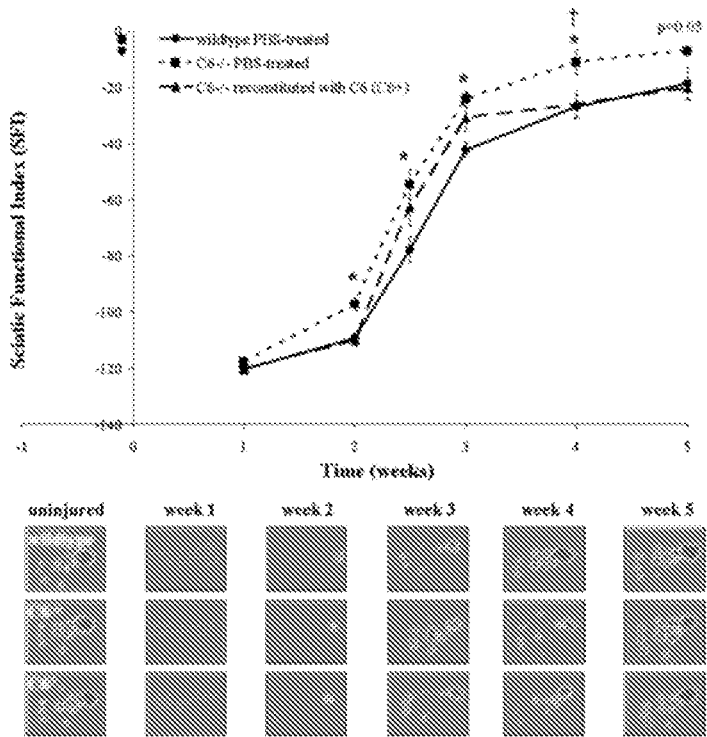
FIG. 8. Recovery of function. (a) Sciatic Functional Index (SFI) and footprints after sciatic nerve crush injury (time=0) in wildtype (n=8), C6−/− (n=8) and C6+ (n=8) rats showing recovery of motor function over a period of 5 weeks post-injury. Control levels are near 0 whereas values near −140 indicate complete loss of function (week 1). The asterisks (*) refers to significant differences between the wildtype and C6−/− group of rats whereas the cross (†) refers to significant differences between C6−/− and C6+ group of rats with $p\leq0.05$ determined by two way ANOVA test with Bonferroni correction. The wider toe spread in the C6−/− footprint (week 4) compared to the wildtype and C6+ footprints indicates increased muscle strength. (b) Footflick analysis after sciatic nerve crush injury (time=0) in wildtype (n=8), C6−/− (n=8) and C6+ (n=8) rats showing recovery of sensory function over a period of 5 weeks post-injury. Values are expressed as percentage of control levels (100% function). The asterisks (*) refers to significant differences between the wildtype and C6−/− group of rats whereas the cross (†) refers to significant differences between C6−/− and C6+ group of rats with $p\leq0.05$ determined by two way ANOVA test with Bonferroni correction.
Figure 8B:
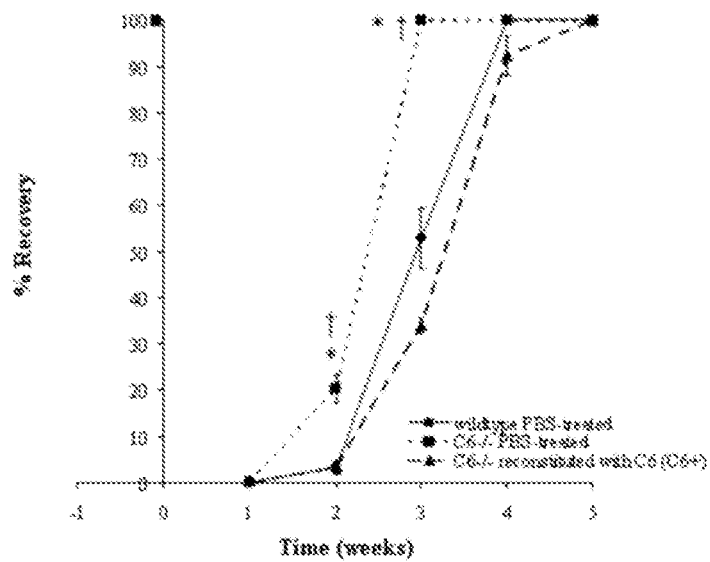
Figure 9:
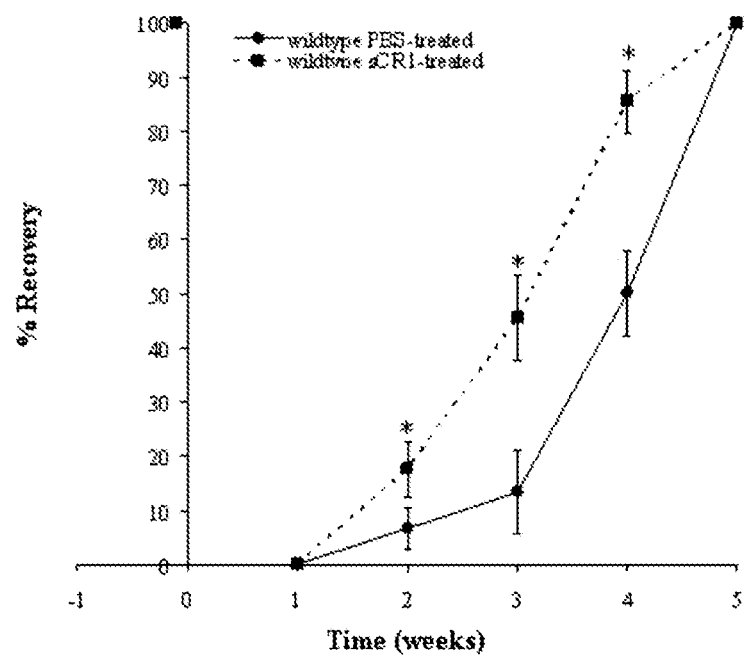
FIG. 9. Recovery of sensory function of C inhibited rats. Footflick analysis after sciatic nerve crush injury (time=0) in wildtype PBS- (n=6) and sCR1- (n=6) treated rats showing recovery of sensory function over a period of 5 weeks post-injury. Values are expressed as percentage of control levels (100% function). The asterisks (*) refers $p\leq0.05$ determined by two way ANOVA test with Bonferroni correction.

Recovery of motor function was monitored every week after injury by measuring the sciatic functional index (SFI) calculated from the rats walking pattern (Hare et al., 1992). At 1 week post-injury, none of the animals used the foot of the injured leg to walk, failing to produce a footprint on the walking platform, suggesting complete loss of muscle innervation in the leg. From week 2 post-injury and throughout the whole study $C6^{-/-}$ rats (n=16) produced an SFI significantly higher than wildtype animals (n=16; p≤0.05, two way ANOVA) (FIG. 8a). A higher SFI results from an increase in the print length and toe spreading parameters and indicates re-innervation of the calf and small foot muscles, respectively. Reconstitution of the $C6^{-/-}$ rats with purified C6 protein (C6+) significantly reduced the SFI (n=8; p≤0.05, two way ANOVA) to wildtype levels at week 4 and 5 post-injury. These data demonstrate that C6 deficiency in rats results in a faster recovery of motor function compared to wildtype. Recovery of sensory function was assayed with the footflick test. At 1 week post-injury, none of the animals retracted their paw when the footsole was stimulated by an electric shock at 0.5 mA, suggesting complete loss of sensory innervation. From week 2 to week 3 post-injury, the $C6^{-/-}$ rats showed 20-50% greater recovery of sensory function compared to wildtype (n=16) and C6+ (n=8) rats (p≤0.05, two way ANOVA). The sensory function did not differ between groups at weeks 4 and 5 post-injury (FIG. 8b). Similarly, animals treated with sCR1 showed a faster (10-30% increase, n=6; p<0.05, two way ANOVA) recovery of sensory function than the PBS-treated rats (n=6) between weeks 2 and 4 post-injury (FIG. 9). These data indicate that both C deficiency and inhibition of C activation accelerate and improve the return of sensory innervation to the footsole after sciatic crush injury.

Figure 10:
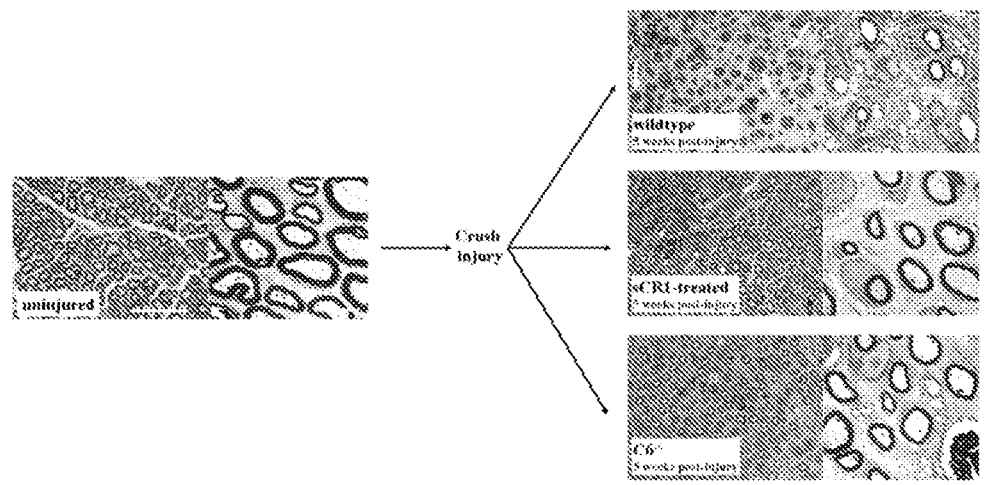
FIG. 10. Pathology. Thionine staining and electron microscopy of cross-sections of the distal ends of tibial nerves from uninjured (n=6), wildtype (n=5), C6−/− (n=5) and sCR1-treated (n=6) rats at 5 weeks following the crush injury. Note the presence of regenerative clusters of small caliber, thinly myelinated axons in the wildtype nerve (arrows →) whereas single large caliber axons are present in the C6−/− and sCR1-treated nerves, similarly to the uninjured control. Bar is 50 μm (light microscopy, left panels) and 10 μm (electron microscopy, right panels).

To follow the histological regeneration of the damaged nerve, we analyzed the tibial nerve at different time points. The regenerative process is marked by the occurrence of regenerative clusters of axons which are sprouts of the originally injured axon. Initially, the axon sprouts reside within a single Schwann cell cytoplasm but they are later separated by radial sorting. Once the 1:1 relationship between Schwann cell and axon is established, the pro-myelinating SC starts to ensheath the axon to form myelin and the basal lamina tube. At this stage, the regenerative clusters appear as groups of small caliber, thinly myelinated axons within adjacent Schwann cells (FIG. 10, arrows). Once one axon has reached its target, the rest of the axon sprouts are eliminated while the remaining axon increases in size. On histological sections at 5 weeks post-injury, untreated wildtypes and the PBS vehicle-treated controls showed regenerative clusters of small caliber thinly myelinated axons in contrast to $C6^{-/-}$ and sCR1-treated animals where regenerative clusters were absent confirming a faster recovery when C is inhibited or absent (FIG. 10). The frequency of high caliber (>8 µm) myelinated fibers was increased in the $C6^{-/-}$ (0.59±0.20%, n=5) and sCR1-treated (0.58±0.11%, n=6) animals compared to the untreated wildtypes (0.05±0.02; n=5), the C6+ (0.06±0.01; n=3) and the PBS vehicle-treated (none; n=6) controls at 5 weeks post-injury whereas no difference in the frequency of low (<4 µm) and intermediate (4-8 µm) caliber myelinated fibers was found. The myelin thickness was not altered between groups of animals (g-ratio of 0.69±0.01, n=5, wildtype; 0.65±0.02, n=5, $C6^{-/-}$; 0.65±0.01, n=3, C6+; 0.70±0.01, n=6, sCR1-treated; 0.66±0.003, n=6, PBS vehicle-treated) (data not shown).

Taken together, these data show that axonal regeneration and functional recovery after peripheral nerve injury are enhanced in the absence of C6 or when C activation is inhibited by sCR1. Thus the ability to form MAC is a negative determinant of nerve recovery.

Functional recovery after axonal crush injury requires axons to re-enter the Schwann cell tubes injured at the crush site. Once in the distal stump, the axons need to re-navigate the paths followed before injury and generate specific synapse with exactly the same muscle fiber they had previously innervated. In this task they are guided by attractive and repulsive molecular cues (Tessier-Lavigne and Goodman, 1996; Yu and Bargmann, 2001) but recent evidence showed that physical factors also play a key role (Nguyen et al., 2002). Thus, maintenance of intact endoneurial tubes could be of high importance for the regenerating adult peripheral nerve.

Blockade of C activation, and particularly MAC formation, reduces tissue damage during nerve degeneration, appears to rescue the architecture necessary for the guidance of the axon and resulting in more efficient regeneration and recovery of function. Functional improvement in the absence of increased myelin sheath thickness can be explained by the increase in the number of large caliber fibers.

A wealth of evidence over the last decade points to a possible beneficial role of macrophages during recovery (Kiefer et al., 2001). Later after injury, macrophages secrete anti-inflammatory cytokines which are involved in resolving the inflammatory process. Once the inflammation terminates, macrophages contribute to Schwann cell proliferation and survival, remyelination and recovery through the secretion of growth and differentiation factors. We have shown that, early after injury, C inhibition markedly reduces infiltration of endoneurial macrophages (5-fold increase, compared to 25-fold in the absence of C inhibition) (Ramaglia et al., 2007). We postulated that this is due to the proliferation of the resident macrophage population while little contribution comes from the haematogenous macrophages. It is possible that we separated the detrimental effect of the haematogenous macrophages from the beneficial effect which can be exerted by the endoneurial population.

Our findings open the door to a novel therapeutic approach in which blockade of the C cascade, or selective inhibition of MAC, promotes regeneration after traumatic injury and in peripheral neuropathies and neurodegenerative diseases where C-dependent nerve damage has been reported.

5.1.2 Administration of sCR1 or Cetor for Inhibition Studies

Recombinant soluble complement receptor 1 (sCR1) was obtained as previously described (Piddlesden et al., 1994). Complement C1 inhibitor (Cetor) was kindly provided by Sanquin (Amsterdam, The Netherlands). sCR1 was administered i.p. in twelve (12) rats at a dose of 15 mg/kg/day. Cetor was administered i.v. in six (6) rats at a dose of 50 U/rat/day. Twelve (12) rats were treated with equal volumes of vehicle (PBS) alone. The treatment was given one day before the crush injury (day −1) and every 24 hours (day 0, 1, 2) until the nerves were removed at 3 days post-injury. Ten (10) rats were treated either with sCR1 (6) or with PBS (4) up to 6 days post-injury (day −1, 0, 1, 2, 3, 4, 5, 6) and the nerves were removed 1 day after the end of the treatment (day 7).

5.1.3 Hemolytic Assay and ELISA

Blood samples from PBS- and sCR1-treated rats were collected from the tail vein one day before the crush injury (day −1) and every following day (day 0, 1, 2) until the animals were sacrificed at 3 days after the injury. In the group treated up to 6 days, additional blood samples were collected at day 3, 5 and 7 after injury. All samples were collected immediately before each injection of treatment. Plasma was separated and stored at −80° C. until used to monitor sCR1 inhibitory activity via standard complement hemolytic assay (Morgan, 2000).

Plasma levels of sCR1 were measured using ELISA assay as previously described (Mulligan et al., 1992) using serial dilutions assayed in duplicates.

5.1.4 Nerve Crush Injury and Tissue Processing

TABLE 1

Plasma haemolytic activity (% CH50).

| | Day −1 | Day 0 (crush) | Day 1 | Day 2 | Day 3 | Day 4 | Day 5 | Day 7 |
|---|---|---|---|---|---|---|---|---|
| Wildtype PBS-treated | 91.6 ± 1.0 | 91.7 ± 1.1 | 81.2 ± 1.7 | 89.5 ± 1.5 | 86.1 ± 1.4 | n.d. | 82.1 ± 1.7 | 90.8 ± 4.1 |
| C6 deficient PBS-treated | 14.0 ± 0.1 | n.d. | n.d. | 12.8 ± 0.2 | n.d. | 13.5 ± 0.3 | n.d. | 15.7 ± 0.4 |
| C6 deficient C6-treated (C6$^+$) | 14.0 ± 0.1 | n.d. | n.d. | 78.5 ± 0.9* | n.d. | 76.9 ± 0.8* | n.d. | 78.5 ± 1.6* |
| Wildtype sCR1-treated | 87.4 ± 0.6 | 36.8 ± 1.1* | 27.2 ± 0.9* | 27.2 ± 3.6* | 27.9 ± 0.3* | n.d. | 29.6 ± 1.7* | 33.4 ± 2.9* |

C dependent hemolysis in serum from wildtype PBS-treated,
C6$^{−/−}$ PBS-treated and C6$^{−/−}$ reconstituted with purified human C6 (C6$^+$) rats and sCR1-treated rats. Treatment started 1 day (day −1) before the injury (day 0) and it was repeated every day until 1 week.
Plasma was collected at days −1, 2, 4, and 7 immediately before the treatment.
Values are means ± S.D. of six to eight animals per group per time point.
Statistical significance (*) refers to p ≤ 0.001 determined by a two way ANOVA test with Bonferroni correction.
n.d., not determined.

Example 5

5.1 Materials and Methods 5.1.1 Animals

This study was approved by the Academic Medical Center Animal Ethics Committee and complies with the guidelines for the care of experimental animals.

Male 12 weeks old PVG/c were obtained from Harlan (UK). The animals weighed between 200 g and 250 g and were allowed acclimatization for at least two weeks before the beginning of the study. Animals were kept in the same animal facility during the entire course of the experiment and monitored for microbiological status according to the FELASA recommendations. Animals were housed in pairs in plastic cages. They were given rat chow and water ad libitum and kept at a room temperature of 20° C. on a 12 hours:12 hours light:dark cycle.

All the surgical procedures were performed aseptically under deep isoflurane anesthesia (2.5% Vol isoflurane, 1 L/min O$_2$ and 1 L/min N$_2$O). The left thigh was shaved and the sciatic nerve was exposed via an incision in the upper thigh. The nerve was crushed for three 10 s periods at the level of the sciatic notch using smooth, curved forceps (No. 7). The crush site was marked by a suture which did not constrict the nerve. On the right side, a sham surgery was performed which exposed the sciatic nerve but did not disturb it. A suture was also placed. The muscle and the skin were closed with stitches. Following the crush, the rats were allowed to recover for 3 days (PBS-treated n=8; sCR1-treated n=6; Cetor-treated n=6) and 7 days (PBS-treated n=4; sCR1-treated n=6).

All the animals were intracardially perfused with 4% paraformaldehyde in piperazine-N—N'-bis(2-ethane sulphonic acid) (PIPES) buffer (pH 7.6). Left and right sciatic nerves were removed from each animal and one segment of 5 mm length was collected distally from the crush site. Each segment was conventionally processed into paraffin wax for immunohistochemistry.

5.1.5 Immunohistochemistry

Paraffin wax sections were stained using a three-step immunoperoxidase method. All the incubations were performed at room temperature (RT). Following deparaffination and rehydration, endogenous peroxidase activity was blocked with 1% $H_2O_2$ in methanol for 20 min. In all cases, microwave antigen retrieval was used (800 W for 3 min followed by 10 min at 440 W in 10 mM Tris/1 mM EDTA pH 6.5). To block the non-specific binding sites, slides were incubated in 10% normal goat serum (NGS) in Tris buffered saline (TBS) for 20 min. Following incubation in the appropriate primary antibody diluted in 1% BSA (see Table 2) for 90 min, sections were incubated for 30 min in biotinylated goat anti-rabbit or goat anti-mouse IgG from DakoCytomation (Glostrup, DK) diluted 1:200 in 1% BSA and 30 min in horseradish peroxidase labeled polystreptavidin (ABC-complex, DAKO). To visualize peroxidase activity, the slides were incubated in 0.05% 3-amino-9-ethylcarbazole in acetate buffer (pH 5) for 5 min followed by a 30 sec counterstaining with hematoxylin and mounted in gelatin. Sections immunostained with secondary conjugate alone were included with every experiment as negative controls while sections of rat spinal cord and lymph nodes served as positive controls.

Images were captured with a digital camera (Olympus, DP12, The Netherlands) attached to a light microscope (Olympus, BX41, The Netherlands).

TABLE 2

Antibodies, source and dilutions for immunohistochemistry.

| Antibodies | Source | Dilutions |
|---|---|---|
| Monoclonal mouse anti-human Phosphorilated neurofilament (SMI31 clone) | Stemberger (Lutherville, UK) | 1:1000 |
| Polyclonal rabbit anti-human MBP | DakoCytomation (Glostrup, DK) | 1:100 |
| Monoclonal mouse anti-rat CD68 (ED1 clone) | Serotec (Oxford, UK) | 1:100 |
| Polyclonal rabbit anti-rat C9 | B. P. Morgan | 1:300 |
| Polyclonal rabbit anti-human C3c | DakoCytomation (Glostrup, DK) | 1:750 |
| Polyclonal rabbit anti-human C4c | DakoCytomation (Glostrup, DK) | 1:100 |

5.1.6 Quantitative Analysis of Immunohistochemistry

All analyses were performed with the Image Pro Plus version 5.02 (Media Cybernatics, The Netherlands). CD68 (ED1 clone)-immunoreactive cells were scored positive when the CD68 positive signal was associated with nuclei. Thirty non-consecutive sections of sciatic nerve per rat were scored. An average of 3 non-overlapping fields of view including >90% of the entire nerve area was taken for each section. Quantification of the MAC and MBP immunostaining was performed at 40× magnification on two non-overlapping fields per section examined. Ten sections per rat were scored. The surface area stained is expressed as percentage of total area examined.

5.1.7 Protein Extraction and Western Blot Analysis

Frozen sciatic nerves from 2 untreated rats sacrificed at 2 days following the crush injury were homogenized using a pestle and mortar in liquid nitrogen in 20 mmol $l^{-1}$ Tris (pH 7.4), 5 mmol $l^{-1}$ 1,4-dithio-DL-threitol (DTT) and 0.4% SDS and 6% glycerol. The homogenates were centrifuged at 10,000×g, at 2° C. for 10 min. The supernatant fraction was collected and used for protein analysis. Protein concentrations were determined with a DC protein assay kit (Bio-Rad Laboratories, USA), using bovine serum albumin (BSA) as a standard.

Protein extracts (20 μg/sample) were boiled for 5 min, separated by 10% SDS-PAGE and transferred to nitrocellulose membrane overnight at 4° C. Prior to blotting, the nitrocellulose membranes were stained with Ponseau red for 30 sec to verify protein load. The membranes were pre-incubated in 50 mmol $l^{-1}$ TrisHCl containing 0.5% Tween20 (TBST) and 5% non-fat dried milk for 1 hour at RT. Blots were incubated for 2 hours in the polyclonal goat anti-factor Bb (fBb) (Quidel, San Diego, Calif.) diluted in TBST containing 5% non-fat dried milk. Following washing in TBST, the membranes were incubated for 1 hour in polyclonal rabbit anti-goat horseradish peroxidase-conjugated secondary antibody diluted 1:2000 in TBST containing 5% non-fat dried milk. Membranes were washed in TBST for 30 min and immunoreactive bands were detected using enhanced chemiluminescence (ECL, Amersham, Piscataway, N.J., USA). Quantification of the immunoreactive bands was performed using Advanced Image Data Analyzer software v. 3.4 (Raytest, Germany).

5.1.7 Statistical Analysis

Two-way ANOVA with Bonferroni correction was performed to determine statistically significant differences ($p \leq 0.001$). Statistical analysis of the immunoblotting quantification was determined by unpaired t-test ($p \leq 0.05$).

5.2 Results 5.2.1 sCR1 Blocks Complement Activation After Acute Nerve Trauma

Figure 11A:
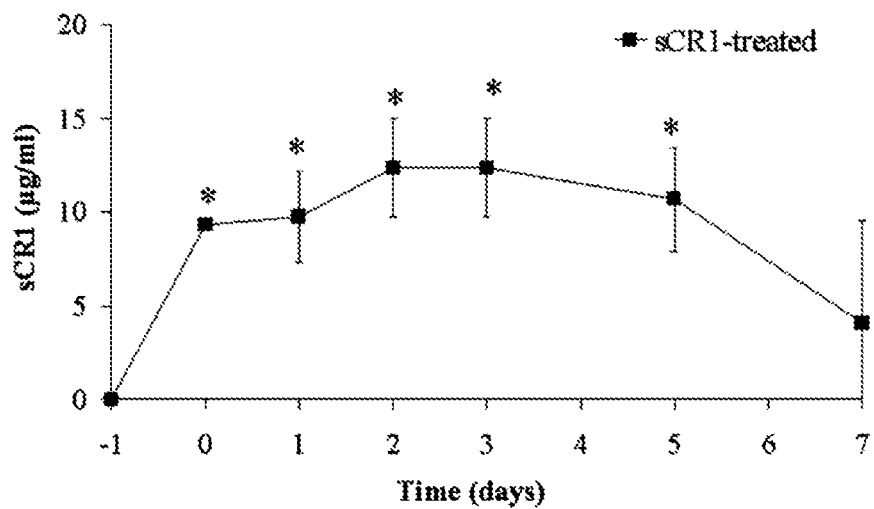
FIGS. 11a and 11b. sCR1 inhibition of complement activation (A) Plasma sCR1 levels in sCR1-treated rats, showing concentration of sCR1 over time with daily treatment. (B) Plasma hemolytic activity of PBS- and sCR1-treated rats, showing decreased activity in the sCR1-treated rats compared to the PBS-treated controls. (A, B) Day 0 is the day of the crush injury. Rats received i.p injections of sCR1 (15 mg/kg/day) or PBS (equal volume) at days (−1, 0, 1, 2, 3, 4, 5 and 6). Blood was collected immediately before each treatment. Data represents mean±SD. Statistical significance is determined by two-way ANOVA with Bonferroni correction (* is $p\leq0.001$).
Figure 11B:
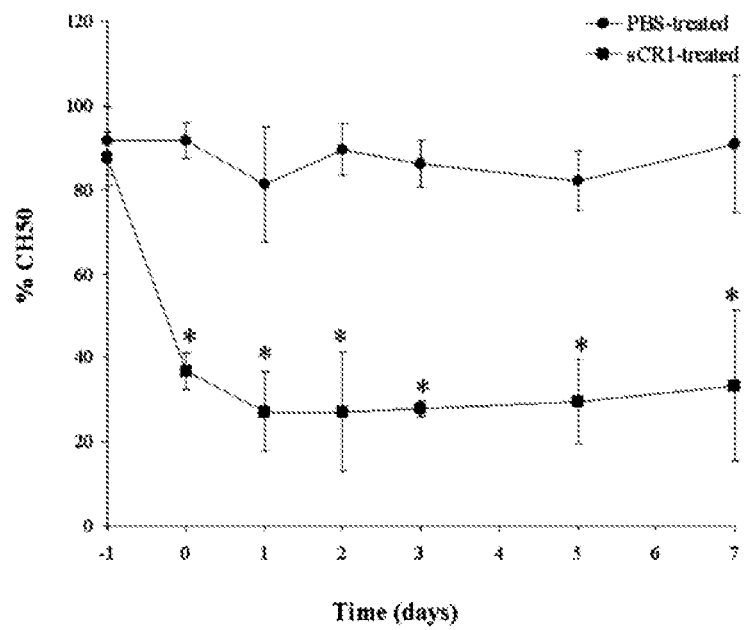

To determine the effects of inhibition of all complement activation pathways on Wallerian degeneration (WD), we treated animals with sCR1. Treatment was started 1 day prior to a crush injury of the sciatic nerve. We measured plasma sCR1 levels and CH50 after daily i.p. injections of either sCR1 at a dose of 15 mg/kg/day or equal volume of vehicle. sCR1 levels increased after the first day of injection and hemolytic complement activity was reduced to about 30% of controls (FIG. 11).

Figure 12:
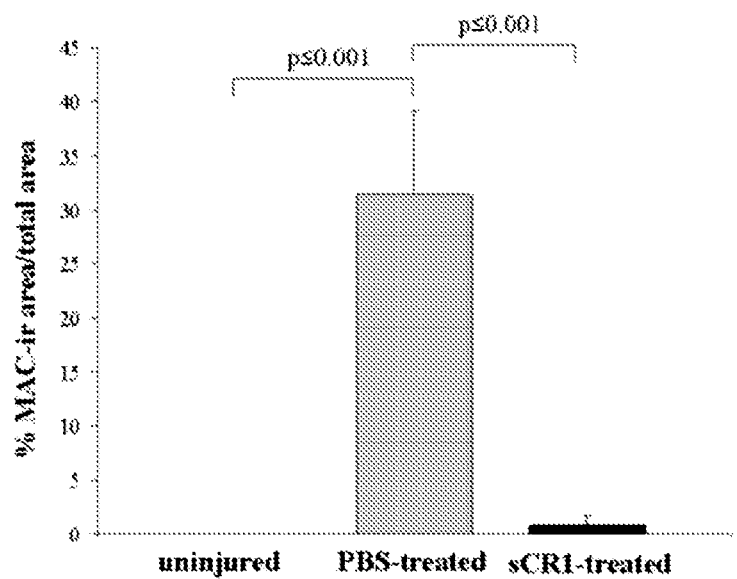
FIG. 12. sCR1 inhibition of complement activation. Quantification of MAC immunoreactivity expressed as percentage of total area scored. Data represents mean±SD. Statistical significance is determined by two-way ANOVA with Bonferroni correction (* is $p\leq0.001$).

The sCR1 treated animals showed inhibition of complement activation in the crushed nerve (FIG. 12). The sCR1-treated nerves showed virtually no MAC deposits (0.8±0.9%) whereas MAC immunoreactivity covered 31.4±7.8% of the total area examined in the nerves of the PBS-treated rats. MAC immunoreactivity was undetectable in the uninjured control nerves. Deposition of C4c and C3c was also prevented in the sCR1-treated nerves whereas high amount of immunoreactivity was detected in the PBS-treated nerves (not shown). These results demonstrate that sCR1 is an effective inhibitor of complement activation after acute nerve trauma.

5.2.2 sCR1 Protects Nerves from Axon Loss at 3 Days Post-Injury

To determine the effects of sCR1-mediated complement inhibition on WD morphological changes of axons and myelin at 3 days post-injury were analyzed.

Neurofilament (SMI31) staining showed that the sciatic nerve of PBS-treated rats had empty and enlarged axonal spaces, delimited by a thin immunoreactive axolemma, and sparse axonal debris within the nerve which are signs of axonal swelling and degradation (data not shown). In contrast, the sCR1-treated rats still showed the typical punctuated appearance of axons, similarly to the uninjured control nerve, demonstrating rescued axonal breakdown at 3 days after injury. Myelin (MBP) immunostaining revealed signs of myelin breakdown in nerves of PBS-treated rats at 3 days following the injury whereas the nerves of sCR1-treated rats showed the typical annulated myelin staining similar to uninjured control nerves, demonstrating rescued myelin degradation at this time point after injury (data not shown). These observations demonstrate that sCR1 protects nerves from axonal degradation and myelin at 3 days post-injury.

Analysis of sciatic nerves of both PBS- and sCR1-treated rats at 7 days post-injury shows axonal and myelin breakdown in both groups of animals, demonstrating that WD was delayed but not prevented in sCR1-treated nerves following the crush injury (data not shown).

Quantification of the MBP staining showed significant lower immunoreactivity in the crushed nerves compared to the uninjured nerves (21.7±3.5%). The amount of MBP immunoreactive debris differed between nerves of PBS- and sCR1-treated rats. The PBS-treated nerves showed significantly less percentage of MBP immunoreactive area (2.1±1.3%) compared to the sCR1-treated nerves (7.6±1.0%). This demonstrates that clearance of myelin debris is delayed in the sCR1-treated nerves.

Figure 13:
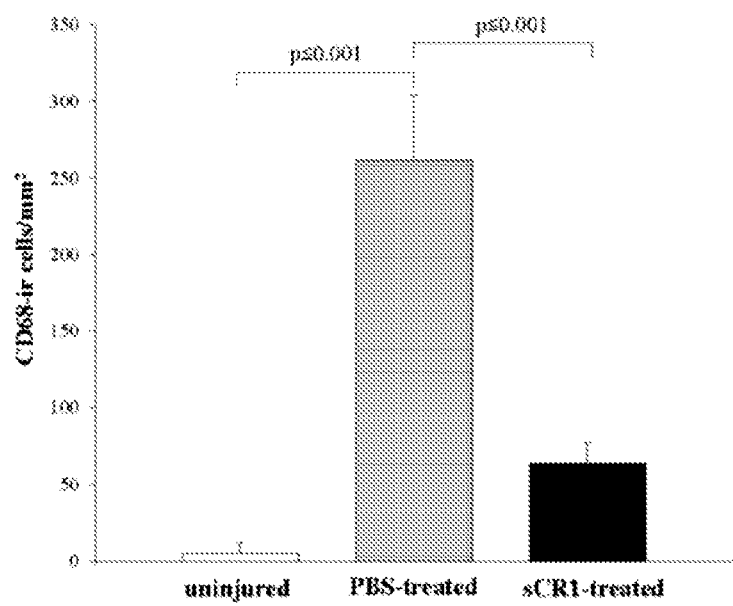
FIG. 13. Analysis of macrophages. Quantification of CD68-ir cells in non-consecutive sections of sciatic nerves, showing a high number of cells in the PBS-treated nerves and slight increase in the sCR1-treated nerves, compared to the uninjured nerve. Data represents mean±SD. Statistical significance is determined by two-way ANOVA with Bonferroni correction.

5.2.3 sCR1 Prevents Macrophage Accumulation and Activation at 3 Days Post-Injury We monitored accumulation and morphological changes of macrophages because complement activation mediates macrophages recruitment and activation. We used the CD68 antibody (ED1 clone), a lysosomal marker, as marker for their metabolic state. A few CD68 immunoreactive cells were found in the control uninjured nerve (5.3±1.7 cells/mm$^2$). The number increased to 261.2±10.7 cells/mm$^2$ in the nerves of the PBS-treated rats at 3 days post-injury while the nerves from the sCR1-treated rats showed a milder increase (63.1±4.7 cells/mm$^2$) (FIG. 13).

The nerves of the PBS-treated rats showed large and asymmetrical CD68 immunoreactive cells (average size 103.6±71.8 µm$^2$) at 3 days post-injury, while small and round cells (average size 22.8±14.1 µm$^2$) were detected in the nerves of the sCR1-treated rats, a size and shape similar to that seen in the uninjured control nerves (average size 18.8±6.6 µm$^2$) (data not shown).

Figures 14A, 14B, 14C:
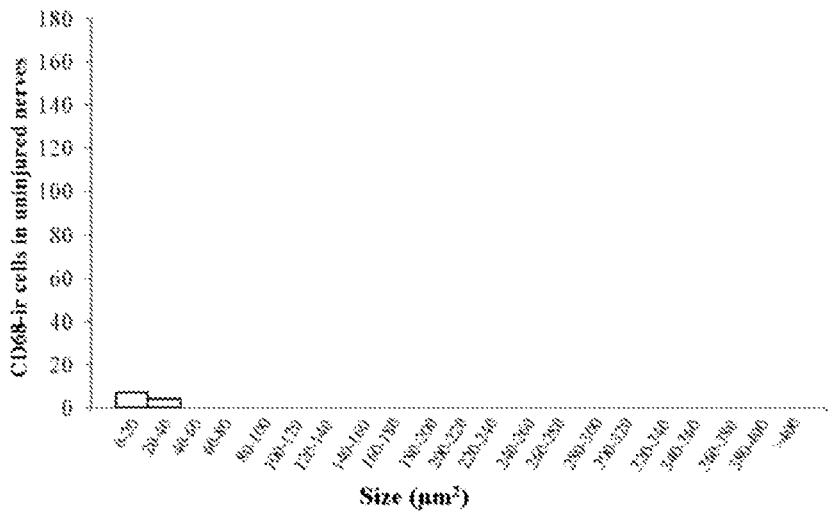
FIG. 14. Analysis of macrophages. Size distribution of CD68-ir cells sciatic nerves from uninjured nerve (a), PBS-treated (b) and sCR1-treated (c) nerves at 3 days post-injury. Note the shift in the peak of CD68-ir cell size distribution from a size of 0-40 μm² in the uninjured and sCR1-treated nerves to a size of 40-120 μm² in the PBS-treated nerves.

Determination of the CD68 immunoreactive cell size distribution was performed on 11 cells in the uninjured nerves, 778 cells in the PBS-treated nerves and 294 cells in the sCR1-treated nerves. Cell size distribution showed high variability in the PBS-treated nerves with cell dimension ranging from 20 to more than 400 µm$^2$ with a large population of cells of about 60 µm$^2$. In contrast, the sCR1-treated nerves showed cell dimension ranging from 0 to 40 µm$^2$, similar to the size of cells found in the uninjured control nerves (FIG. 14). The colocalization of MBP and CD68 shows macrophages engulfing myelin in the PBS-treated nerves while small resting macrophages are visible between the morphologically intact myelin sheaths of the uninjured and sCR1-treated nerves (data not shown). These results show that macrophages are activated in the PBS-treated nerves but not in the sCR1-treated ones.

5.2.4 Activation of the Alternative Pathway after Acute Nerve Trauma

Figure 15A:
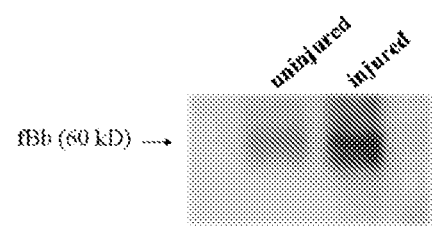
FIG. 15. Analysis of alternative pathway activation. (a) Western blotting analysis of rat sciatic nerves at 2 days post-injury, showing higher amount of cleaved fBb protein in the injured nerves compared to the uninjured controls. (b) Relative quantification of fBb immunoreactive bands. The fBb immunoreactivity in uninjured controls is defined as 1.0 fold relative expression. Values are normalized to total protein load and represent mean±SD of three blots. Statistical significance is determined by unpaired t-test.
Figure 15B:
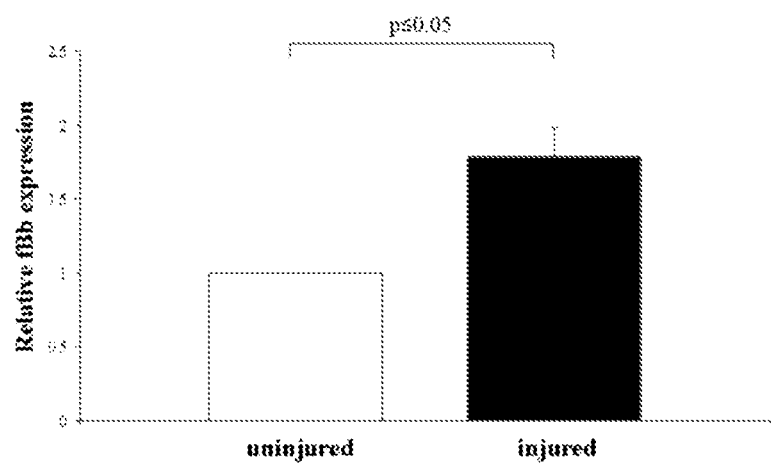

We have found that the classical pathway of the complement system is activated after acute nerve trauma. To determine whether the alternative pathway is also triggered by a crush injury of the sciatic nerve, we measured the expression level of Bb, the 60 kD protein fragment which results from the cleavage of factor B. Low levels of Bb immunoreactivity were detected in protein extracts of uninjured rat nerves, whereas a near two fold increase (1.8±0.2) was seen at 2 days following the crush injury (FIG. 15 A, B). These results indicate that the alternative pathway loop is triggered after acute nerve trauma, generating more cleaved fB.

5.2.5 Effects of C1 Inhibitor on WD

To determine whether the alternative pathway is sufficient to cause pathology we treated rats with C1 inhibitor (Cetor). Inhibiting the classical and lectin pathways with the complement C1 inhibitor, Cetor, would allow us to determine the contribution of the different complement pathways. Cetor dosage was extrapolated from the work of de Smet et al. Immunostaining of the Cetor treated crushed nerves for activation products of the classical pathway (C4c) was negative and thus suggested inhibition of the classical pathway.

Low amounts of MAC immunoreactivity (7.3±2.7% of total area examined) were visible in the nerves of Cetor-treated animals at 3 days post-injury and the staining was mainly localized in the axonal compartment of some fibers (data not shown). The neurofilament (SMI31 clone) staining showed fibers with normal punctuated axonal immunoreactivity and fibers with atypical annulated immunoreactivity outlining enlarged axonal spaces. This demonstrates abnormal distribution of the phosphorylated neurofilament epitope, compatible with neurofilament breakdown (data not shown). These observations suggest an intimate link between MAC deposition and axon loss. The myelin (MBP) staining showed normal annulated myelin morphology (data not shown) and the CD68 staining revealed a number of cells (59.8±28.3 cells/mm$^2$) similar to that observed in the sCR1-treated nerves. In addition the average CD68 immunoreactive cell size (19.1±10.5 µm$^2$) and size distribution determined on 218 cells did not differ from sCR1-treated nerves or uninjured controls (data not shown). The colocalization of MBP and CD68 shows small resting macrophages between the morphologically intact myelin sheaths (data not shown). These results suggest a link between lack of macrophage activation and preserved myelin morphology at 3 days post-injury.

5.3 Discussion

The present invention demonstrates that systemic treatment with sCR1, an inhibitor of classical, lectin and alternative pathways of complement activation, protects from early axon loss and myelin breakdown after peripheral nerve injury.

Daily administration of sCR1 to injured rats prevented both systemic and local complement activation, resulting in blockade of MAC deposition in the nerve. In untreated animals, crush injury leads to a rapid increase of CD68 positive cells which enlarge and phagocytose myelin. In the inhibitor-treated nerves only a slight increase of CD68 positive cells was detectable but they failed to enlarge. This appears to be due to the proliferation and differentiation of the endoneurial macrophage population which occurs already at 2 days after injury (Mueller et al., 2001). Both long-term and short-term resident macrophages newly express the lysosomal ED1 antigen and have the potential to phagocytose myelin (Leonhard et al., 2002). However, this is a complement-mediated event (Bruck W and Friede, 1991). Since complement activation is inhibited in the sCR1-treated nerves, complement opsonins are not deposited on the nervous tissue hampering target recognition and preventing myelin phagocytosis. In addition, complement inhibition also results in inefficient chemotaxis, preventing the recruitment of blood-derived macrophages which probably accounts for the additional 4 fold increase observed in the PBS-treated nerve.

Despite the diminished recruitment and activation of macrophages, sCR1 cannot protect the nerve from axonal degradation and myelin breakdown at 7 days post-injury even when hemolytic complement activity is maintained low. Therefore we conclude that inhibition of complement activation only affects the early events of WD. Lack of C4c deposition in the sCR1-treated nerves is a noteworthy finding because sCR1 inhibits the C3 convertase which is downstream of C4 cleavage, thus little effect on C4c deposition would be expected. However, as also noted in previous studies (Piddlesden et al., 1994), blockade of C-mediated damage by sCR1 will also inhibit overall C deposition on damaged tissue, also resulting in undetectable C4c levels.

We demonstrated that, beside the classical pathway, also the alternative pathway is activated following a crush injury of the peripheral nerve. Blockade of the classical (and lectin) pathway of complement with C1 inhibitor (Cetor), a serine protease inhibitor which blocks activation of the C1q-C1r-C1s (and MBL-MASP) complex,[6,10] diminished but did not ablate MAC deposition in the nerve. Since low rate activation of the alternative pathway occurs under physiological conditions and is negatively regulated by complement inhibitors, disruption of membrane bound complement regulatory components at the site of injury could set the alternative pathway out of control, generating more C3 convertase and leading to MAC deposition. In addition, we cannot rule out that low levels of C3b, which would accumulate during activation of the classical pathway, could escape inhibition by Cetor forming low levels of C5 convertase and acting as substrate for the alternative pathway to further amplify activation. Partial blockade of complement activation results in reduced C3 deposition which reduces macrophage accumulation and prevents their activation while low amounts of MAC are still deposited in the nerve. Interestingly, this is sufficient to cause marked axonal injury (but not much myelin degradation), emphasizing the sensitivity of the axons to MAC-induced damage. This also suggests that myelin loss is an indirect effect of axon loss and it requires macrophages to target the opsonised surface, become activated, strip and degrade the myelin.

Our data show that even low levels of MAC deposition, occurring with C1 inhibitor treatment, are sufficient to cause marked axonal damage.

This invention demonstrates that C-inhibitors protect the peripheral nerve from early axonal degradation and myelin breakdown due to a mechanical injury. Previous studies on demyelinating diseases of the PNS, such as Guillan Barré Syndrome, have been performed on animal models immunized with peripheral nerve myelin to induce the disease phenotype, making their findings directly applicable to diseases where an antigen-antibody complex is likely to mediate complement activation. In WD of the peripheral nerve after a crush injury, complement activation occurs in an antibody-independent manner, directly targeting epitopes on damaged axons and myelin. Thus, the data show that C-inhibitors are also promising tools in the treatment of non-autoimmune diseases, such as inherited peripheral neuropathies, where a secondary role of the immune system superimposed to the primary genetic defect has recently emerged (reviewed in Martini R and Toyka, 2004).

REFERENCES

Baichwal R R, Bigbee J W, DeVries G H (1988) Macrophage-mediated myelin-related mitogenic factor for cultured Schwann cells. Proc Natl Acad Sci USA 85:1701-1705.
Bedi K S, Winter J, Berry M, Cohen J (1992) Adult rat dorsal root ganglion neurons extend neurites on predegenerated but not on normal peripheral nerves in vitro. Eur J Neurosci 4:193-200.
Bhole D and Stahl G L (2004) Molecular basis for complement component 6 (C6) deficiency in rats and mice. Immunobiology 209:559-68.
Bruck, W (1997) The role of macrophages in Wallerian degeneration. Brain Pathol 7:741-752.
Bruck W and Friede R L (1991) The role of complement in myelin phagocytosis during PNS wallerian degeneration. J Neurol Sci 103: 182-187.
Canfield and Morrison (1991) The binding affinity of human IgG for its high affinity Fc receptor is determined by multiple amino acids in the CH2 domain and is modulated by the hinge region. J. Exp. Med. 173: 1483-1491.
Dailey A T, Avellino A M, Benthem L, Silver J, Kliot M. (1998) Complement depletion reduces macrophage infiltration and activation during Wallerian degeneration and axonal regeneration. J Neurosci 18(17):6713-22.
De Koning P, Brakkee J H, Gispen W H (1986) Methods for producing a reproducible crush in the sciatic and tibial nerve of the rat and rapid and precise testing of return of sensory function. Beneficial effects of melanocortins. Journal of Neurological Sciences 74:237-246.
Evans M J, Hartman S L, Wolff D W, Rollins S A, Squinto S P (1995) Rapid expression of an anti-human C5 chimeric Fab utilizing a vector that replicates in COS and 293 cells. J. Immunol. Meth 184: 123-138.
Feasby T E, Gilbert J J, Hahn A F, Neilson M (1987) Complement depletion suppresses Lewis rat experimental allergic neuritis. Brain Res 419:97-103.
Fung M, Lu M, Fure H, Sun W, Sun C, Shi N Y, Dou Y, Su J, Swanson X, Mollnes T E (2003) Pre-neutralization of C5a-mediated effects by the monoclonal antibody 137-26 reacting with the C5a moiety of native C5 without preventing C5 cleavage. Clin Exp Immunol 133(2):160-9.
Glass J D. Wallerian degeneration as a window to peripheral neuropathy (2004) J Neurol Sci 220:123-4.
Griffin J W, George R, Lobato C, Tyor W R, Yan L C, Glass J D (1992) Macrophage responses and myelin clearance during Wallerian degeneration: relevance to immune-mediated demyelination. J Neuroimmunol 40:153-166.
Hammerling (1981) Monoclonal Antibodies and T-Cell Hybridomas. Elsevier, N.Y. 563-681
Hare G M T, Evans P J, MAckinnon S E, Best T J, Bain J R, Szalai J P and Hunter R T (1992). Walking track analysis: a long term assessment of peripheral nerve recovery. Plastic and Reconstructive Surgery 89:(2)251-258.
Harlow (1998) Antibodies: A Laboratory Manual, Cold Spring Harbor Laboratory Press, 2nd ed.
Hourcade D, Miesner D R, Atkinson J P, Holers V M (1988) Identification of an alternative polyadenylation site in the human C3b/C4b receptor (complement receptor type 1) transcriptional unit and prediction of a secreted form of complement receptor type 1. J. Exp. Med. 168:1255-1270.
Jerosch-Herold (2005) Assessment of sensibility after nerve injury and repair: a systematic review of evidence for validity, reliability and responsiveness of tests. Hand Surg 30(3):252-64.
Jung S, Toyka K V, Hartung H P (1995) Soluble complement receptor type 1 inhibits experimental autoimmune neuritis in Lewis rats. Neurosci Lett 200:167-70.
Kacani L, Bánki Z, Zwirner J, Schennach H, Bajtay Z, Erdei A, Stoiber H, Dierich M P (2001) C5a and C5a(desArg) enhance the susceptibility of monocyte-derived macrophages to HIV infection. J. Immunol. 166:3410-3415.
Kiefer R, Kieseier B C, Stoll G, Hartung H P (2001) The role of macrophages in immune-mediated damage to the peripheral nervous system. Prog Neurobiol. 64(2):109-127.

King R H M. Atlas of peripheral nerve pathology. New York: Oxford University Press Inc., 1999.

Klickstein L B, Wong W W, Smith J A, Weis J H, Wilson J G, Fearon D T (1987) Human C3b/C4b receptor (CR1). Demonstration of long homologous repeating domains that are composed of the short consensus repeats characteristics of C3/C4 binding proteins. J. Exp. Med. 165: 1095-1112

Klickstein L B, Bartow T J, Miletic V, Rabson L D, Smith J A, Fearon D T. (1988) Identification of distinct C3b and C4b recognition sites in the human C3b/C4b receptor (CR1, CD35) by deletion mutagenesis. J. Exp. Med. 168:1699-1717.

Leinhase I, Holers V M, Thurman J M, Harhausen D, Schmidt C H, Pietzcker M, Taha M E, Rittirsch D, Huber-Lang M, Smith W R, Ward P A, Stahel P F (2006) Reduced neuronal cell death after experimental brain injury in mice lacking a functional alternative pathway of complement activation. BMC Neurosci 14; 7(1):55.

Leonhard C, Muller M, Hickey W F, Ringelstein E B, and Kiefer R (2002) Lesion response of long-term and recently immigrated resident endoneurial macrophages in peripheral nerve explant cultures from bone marrow chimeric mice. Eur J Neurosci 16: 1654-1660.

Lindholm D, Heumann R, Meyer M, Thoenen H (1987) Interleukin-1 regulates synthesis of nerve growth factor in non-neuronal cells of rat sciatic nerve. Nature 330:658-659.

Martini R and Toyka K V (2004) Immune-mediated components of hereditary demyelinating neuropathies: lessons from animal models and patients. Lancet Neurol 3: 457-465.

McAleer, M A and Sim, R B (1993) Activators and Inhibitors of Complement. Kluwer Academic Publishers, Dordrecht, ed R B Sim, p. 1-15.

Mead R J, Singhrao S K, Neal J W, Lassmann H, Morgan B P (2002) The membrane attack complex of complement causes severe demyelination associated with acute axonal injury. J Immunol 168: 458-465.

Morgan B P (2000) Measurement of complement hemolytic activity, generation of complement-depleted sera, and production of hemolytic intermediates. Methods Mol Biol 150: 61-71.

Mueller M, Wacker K, Ringelstein E B, Hickey W F, Imai Y, and Kiefer R (2001) Rapid response of identified resident endoneurial macrophages to nerve injury. Am J Pathol 159: 2187-2197.

Mulligan M S, Yeh C G, Rudolph A R, and Ward P A (1992) Protective effects of soluble CR1 in complement- and neutrophil-mediated tissue injury. J Immunol 148: 1479-1485.

Nguyen Q T, Sanes J R, Lichtman J W (2002) Pre-existing pathways promote precise projection patterns. Nat. Neurosci. 5(9):861-7.

Oppermann M, Raedt U, Hebell T, Schmidt B, Zimmermann B, Götze O. (1993) Probing the human receptor for C5a anaphylatoxin with site-directed antibodies. Identification of a potential ligand binding site on the $NH_2$-terminal domain. J. Immunol. 151(7):3785-3794.

Piddlesden S J, Storch M K, Hibbs M, Freeman A M, Lassmann H, and Morgan B P (1994) Soluble recombinant complement receptor 1 inhibits inflammation and demyelination in antibody-mediated demyelinating experimental allergic encephalomyelitis. J Immunol 152: 5477-5484.

Pulito V L, Roberts V A, Adair J R, Rothermel A L, Collins A M, Varga S S, Martocello C, Bodmer M, Jolliffe L K, Zivin R A. (1996) Humanization and molecular modeling of the anti-CD4 monoclonal antibody, OKT4A. J. Immunol. 156: 2840-2850.

Quigg R J, Kozono Y, Berthiaume D, Lim A, Salant D J, Weinfeld A, Griffin P, Kremmer E, Holers V M. (1998) Blockade of antibody-induced glomerulonephritis with Crry-Ig, a soluble murine complement inhibitor. J. Immunol 160:4553-9.

Ramaglia V, King R H, Nourallah M, Wolterman R, de Jonge R, Ramkema M, Vigar M A, van der Wetering S, Morgan B P, Troost D, Baas F (2007) The membrane attack complex of the complement system is essential for rapid Wallerian degeneration. J Neurosci 18; 27(29):7663-72.

Reid K B M and Law A (1988) Complement. IRL Press, Oxford.

de Smet B J, de Boer J P, Agterberg J, Rigter G, Bleeker W K, and Hack C E (1993) Clearance of human native, proteinase-complexed, and proteolytically inactivated C1-inhibitor in rats. Blood 81: 56-61.

Riechmann L, Clark M, Waldmann H, Winter G (1988) Reshaping human antibodies for therapy. Nature 332: 323-327.

Tessier-Lavigne M and Goodman C S (1996) The molecular biology of axon guidance. Science 15; 274(5290):1123-1133.

Vriesendorp F J, Flynn R E, Pappolla M A, Koski C L (1995) Complement depletion affects demyelination and inflammation in experimental allergic neuritis. J Neuroimmunol 58:157-165.

Waller, A (1850) Experiments on the section of glossopharyngeal and hypoglossal nerves of the frog and observations on the alterations produced thereby in the structure of their primitive fibers. Phil Trans R Soc Lond. 140, 423-429.

Weisman H F, Bartow T, Leppo M K, Boyle M P, Marsh H C, Jr., Carson G R, Roux K H, Weisfeldt M L, and Fearon D T (1990) Recombinant soluble CR1 suppressed complement activation, inflammation, and necrosis associated with reperfusion of ischemic myocardium. Trans Assoc Am Physicians 103: 64-72.

Wong K H, Coert J H, Robinson P H, Meek M F (2006) Comparison of assessment tools to score recovery of function after repair of traumatic lesions of the median nerve. Scand J Plast Reconstr Surg Hand Surg 40:219-24.

Woodruff T M, Crane J W, Proctor L M, Buller K M, Shek A B, de Vos K, Pollitt S, Williams H M, Shiels I A, Monk P N, Taylor S M (2006) Therapeutic activity of C5a receptor antagonists in a rat model of neurodegeneration. FASEB J 20: 1407-1417.

Xu Y, Oomen R, Klein M H (1994) Residue at position 331 in the IgG1 and IgG4 CH2 domains contributes to their differential ability to bind and activate complement. J. Biol. Chem. 269: 3468-3474.

Yu T W and Bargmann C I (2001) Dynamic regulation of axon guidance. Nat Neurosci 4:1169-1176.

The invention claimed is:

1. A method of promoting functional recovery of damaged or degenerating peripheral nerves in a subject comprising administering to the subject a therapeutically effective amount of a human or humanized monoclonal antibody that binds to C5, wherein the antibody inhibits cleavage of C5 and formation of a membrane attack complex.

2. The method according to claim 1, wherein the subject is suffering from a physical injury of a peripheral nerves.

3. The method according to claim 1, wherein the antibody is administered at or near a site of injury.

4. The method of claim 1, wherein the subject is suffering from injury of the PNS.

5. The method of claim 4, wherein the injury of the PNS is nerve trauma resulting from physical injury.

6. The method of claim 5, wherein the physical injury to the PNS is a traumatic injury.

\* \* \* \* \*

UNITED STATES PATENT AND TRADEMARK OFFICE
CERTIFICATE OF CORRECTION

PATENT NO. : 8,703,136 B2  
APPLICATION NO. : 12/445037  
DATED : April 22, 2014  
INVENTOR(S) : Baas et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1352 days.

Signed and Sealed this  
Twenty-second Day of March, 2016

Michelle K. Lee  
*Director of the United States Patent and Trademark Office*